US012383333B2

United States Patent
Pappone et al.

(10) Patent No.: US 12,383,333 B2
(45) Date of Patent: *Aug. 12, 2025

(54) THERMAL MAPPING CATHETER

(71) Applicant: St. Jude Medical, Cardiology Division, Inc., St. Paul, MN (US)

(72) Inventors: Carlo Pappone, Cernusco Lombardone (IT); Alan de la Rama, Cerritos, CA (US); Gabriele Giuseppe Vicedomini, Brisighella (IT); Cary Hata, Irvine, CA (US); Tho Hoang Nguyen, Huntington Beach, CA (US); Peter Chen, Irvine, CA (US)

(73) Assignee: St. Jude Medical, Cardiology Division, Inc., St. Paul, MN (US)

( * ) Notice: Subject to any disclaimer, the term of this patent is extended or adjusted under 35 U.S.C. 154(b) by 345 days.

This patent is subject to a terminal disclaimer.

(21) Appl. No.: 17/738,388

(22) Filed: May 6, 2022

(65) Prior Publication Data
US 2022/0354568 A1 Nov. 10, 2022

Related U.S. Application Data

(63) Continuation of application No. 15/546,991, filed as application No. PCT/US2016/015449 on Jan. 28, 2016, now Pat. No. 11,350,987.
(Continued)

(51) Int. Cl.
*A61B 18/14* (2006.01)
*A61B 5/287* (2021.01)
*A61B 18/00* (2006.01)

(52) U.S. Cl.
CPC .......... *A61B 18/1492* (2013.01); *A61B 5/287* (2021.01); *A61B 2018/00351* (2013.01);
(Continued)

(58) Field of Classification Search
CPC .......... A61F 7/126; A61B 2018/00797; A61B 18/1492
See application file for complete search history.

(56) References Cited

U.S. PATENT DOCUMENTS

| 4,522,212 A | 6/1985 | Gelinas et al. |
| 5,224,939 A | 7/1993 | Holman et al. |

(Continued)

FOREIGN PATENT DOCUMENTS

| AU | 2015202258 A1 | 5/2015 |
| CN | 101797181 A | 8/2010 |

(Continued)

OTHER PUBLICATIONS

Chockalingam et al., "Fever-Induced Life-Threatening Arrhythmias in Children Harboring an SCN5A Mutation", Pediatrics, vol. 127, No. 1, Jan. 2011, pp. 239-244.
(Continued)

*Primary Examiner* — Michael F Peffley
*Assistant Examiner* — Samantha M Good
(74) *Attorney, Agent, or Firm* — Kilpatrick Townsend & Stockton LLP

(57) ABSTRACT

A catheter is disclosed comprising a catheter shaft including a proximal end and a distal end. A flexible framework can be connected to the distal end of the catheter shaft, wherein the flexible framework includes a plurality of heating electrodes and a temperature sensor. The plurality of heating electrodes can be configured to be heated to a first temperature, the first temperature being lower than which radio frequency ablation is performed. The plurality of heating electrodes can be configured to be heated to a second temperature, the second temperature being a temperature at which radio frequency ablation is performed.

11 Claims, 11 Drawing Sheets

Related U.S. Application Data

(60) Provisional application No. 62/108,945, filed on Jan. 28, 2015.

(52) U.S. Cl.
CPC ............ *A61B 2018/00791* (2013.01); *A61B 2018/00797* (2013.01); *A61B 2018/00839* (2013.01); *A61B 2018/1467* (2013.01); *A61B 2218/002* (2013.01)

(56) References Cited

U.S. PATENT DOCUMENTS

| | | |
|---|---|---|
| 5,380,301 A | 1/1995 | Prichard et al. |
| 5,400,783 A * | 3/1995 | Pomeranz ............... A61N 1/06 600/374 |
| 5,456,254 A | 10/1995 | Pietroski et al. |
| 5,626,136 A | 5/1997 | Webster, Jr. |
| 5,702,438 A | 12/1997 | Avitall |
| 5,715,817 A | 2/1998 | Stevens-Wright et al. |
| 5,715,832 A | 2/1998 | Koblish et al. |
| 5,827,278 A | 10/1998 | Webster, Jr. |
| 5,868,743 A | 2/1999 | Saul et al. |
| 5,876,373 A | 3/1999 | Giba et al. |
| 5,964,757 A | 10/1999 | Ponzi |
| 6,029,091 A | 2/2000 | de la Rama et al. |
| 6,071,282 A | 6/2000 | Fleischman |
| 6,074,379 A | 6/2000 | Prichard |
| 6,123,699 A | 9/2000 | Webster, Jr. |
| 6,171,277 B1 | 1/2001 | Ponzi |
| 6,183,463 B1 | 2/2001 | Webster, Jr. |
| 6,198,974 B1 | 3/2001 | Webster, Jr. |
| 6,210,407 B1 | 4/2001 | Webster |
| 6,254,598 B1 | 7/2001 | Edwards et al. |
| 6,267,746 B1 | 7/2001 | Bumbalough |
| 6,273,404 B1 | 8/2001 | Holman et al. |
| 6,273,886 B1 | 8/2001 | Edwards et al. |
| 6,415,187 B1 | 7/2002 | Kuzma et al. |
| 6,491,681 B1 | 12/2002 | Kunis et al. |
| 6,522,932 B1 | 2/2003 | Kuzma et al. |
| 6,554,794 B1 | 4/2003 | Mueller et al. |
| 6,652,515 B1 | 11/2003 | Maguire et al. |
| 6,658,302 B1 | 12/2003 | Kuzma et al. |
| 6,961,602 B2 | 11/2005 | Fuimaono et al. |
| 7,004,937 B2 | 2/2006 | Lentz et al. |
| 7,027,851 B2 | 4/2006 | Mejia |
| 7,089,045 B2 | 8/2006 | Fuimaono et al. |
| 7,099,712 B2 | 8/2006 | Fuimaono et al. |
| 7,214,220 B2 | 5/2007 | McGlinch et al. |
| 7,217,256 B2 | 5/2007 | Di Palma |
| 7,228,164 B2 | 6/2007 | Fuimaono et al. |
| 7,257,435 B2 | 8/2007 | Plaza |
| 7,412,274 B2 | 8/2008 | Mejia |
| 7,429,261 B2 | 9/2008 | Kunis et al. |
| 7,561,907 B2 | 7/2009 | Fuimaono et al. |
| 7,608,063 B2 | 10/2009 | Le et al. |
| 7,625,365 B2 | 12/2009 | McGlinch et al. |
| 7,666,204 B2 | 2/2010 | Thornton et al. |
| 7,959,601 B2 | 6/2011 | McDaniel et al. |
| 7,985,215 B2 | 7/2011 | Guo et al. |
| 8,103,327 B2 | 1/2012 | Harlev et al. |
| 8,137,321 B2 | 3/2012 | Argentine |
| 8,157,848 B2 | 4/2012 | Zhang et al. |
| 8,221,390 B2 | 7/2012 | Pal et al. |
| 8,271,099 B1 | 9/2012 | Swanson |
| 8,273,016 B2 | 9/2012 | O'Sullivan |
| 8,376,990 B2 | 2/2013 | Ponzi et al. |
| 8,391,947 B2 | 3/2013 | Urman et al. |
| 8,447,377 B2 | 5/2013 | Harlev et al. |
| 8,486,063 B2 | 7/2013 | Werneth et al. |
| 8,500,720 B2 | 8/2013 | Keimel |
| 8,565,894 B2 | 10/2013 | Vetter et al. |
| 8,603,069 B2 | 12/2013 | Selkee |
| 8,608,703 B2 | 12/2013 | Riles et al. |
| 8,649,880 B1 | 2/2014 | Parker, Jr. |
| 8,700,120 B2 | 4/2014 | Koblish |
| 8,706,193 B2 | 4/2014 | Govari et al. |
| 8,744,599 B2 | 6/2014 | Tegg |
| 8,755,861 B2 | 6/2014 | Harlev et al. |
| 8,771,267 B2 | 7/2014 | Kunis et al. |
| 8,777,929 B2 | 7/2014 | Schneider et al. |
| 8,792,962 B2 | 7/2014 | Esguerra et al. |
| 8,814,824 B2 | 8/2014 | Kauphusman et al. |
| 8,814,825 B2 | 8/2014 | Tegg et al. |
| 8,882,705 B2 | 11/2014 | McDaniel et al. |
| 8,894,610 B2 | 11/2014 | Macnamara et al. |
| 8,926,605 B2 | 1/2015 | McCarthy et al. |
| 8,979,841 B2 | 3/2015 | Kunis et al. |
| 8,996,091 B2 | 3/2015 | de la Rama et al. |
| 9,017,308 B2 | 4/2015 | Klisch et al. |
| 9,033,917 B2 | 5/2015 | Magana et al. |
| 9,044,245 B2 | 6/2015 | Condie et al. |
| 9,050,010 B2 | 6/2015 | Bui et al. |
| 9,101,733 B2 | 8/2015 | McDaniel |
| 9,204,929 B2 | 12/2015 | Solis |
| 9,216,056 B2 | 12/2015 | Datta et al. |
| 9,247,990 B2 | 2/2016 | Kauphusman et al. |
| 9,326,815 B2 | 5/2016 | Watson |
| 9,339,631 B2 | 5/2016 | Graham et al. |
| 9,433,751 B2 | 9/2016 | Ponzi et al. |
| 9,433,752 B2 | 9/2016 | Jimenez et al. |
| 9,468,495 B2 | 10/2016 | Kunis et al. |
| 9,486,280 B2 | 11/2016 | Koblish et al. |
| 9,486,282 B2 | 11/2016 | Solis |
| 9,522,035 B2 | 12/2016 | Highsmith |
| 9,532,703 B2 | 1/2017 | Huszar et al. |
| 9,539,413 B2 | 1/2017 | Ogle |
| 9,629,675 B2 | 4/2017 | Kleshinski et al. |
| 9,649,158 B2 | 5/2017 | Datta et al. |
| 9,687,166 B2 | 6/2017 | Subramaniam et al. |
| 9,693,733 B2 | 7/2017 | Altmann et al. |
| 9,694,159 B2 | 7/2017 | Schneider et al. |
| 9,694,161 B2 | 7/2017 | Selkee |
| 9,713,418 B2 | 7/2017 | Huszar et al. |
| 9,788,895 B2 | 10/2017 | Solis |
| 9,820,664 B2 | 11/2017 | Hoitink et al. |
| 9,833,608 B2 | 12/2017 | Masson |
| 9,844,645 B2 | 12/2017 | Pai et al. |
| 9,907,480 B2 | 3/2018 | Basu et al. |
| 9,919,132 B2 | 3/2018 | Tegg et al. |
| 9,986,949 B2 | 6/2018 | Govari et al. |
| 10,004,877 B2 | 6/2018 | Tegg |
| 10,034,637 B2 | 7/2018 | Harlev et al. |
| 10,052,457 B2 | 8/2018 | Nguyen et al. |
| 10,065,019 B2 | 9/2018 | Hamuro et al. |
| 10,099,036 B2 | 10/2018 | Heideman et al. |
| 10,118,022 B2 | 11/2018 | Helgeson et al. |
| 10,136,829 B2 | 11/2018 | Deno et al. |
| 10,143,394 B2 | 12/2018 | Solis |
| 10,322,261 B2 | 6/2019 | Pai et al. |
| 10,384,036 B2 | 8/2019 | Romoscanu |
| 10,398,500 B2 | 9/2019 | Huszar et al. |
| 10,470,682 B2 | 11/2019 | Deno et al. |
| 10,478,247 B2 | 11/2019 | Litscher et al. |
| 10,492,729 B2 | 12/2019 | de la Rama et al. |
| 10,537,259 B2 | 1/2020 | Wu et al. |
| 10,542,899 B2 | 1/2020 | Wu et al. |
| 10,556,091 B2 | 2/2020 | Truhler et al. |
| 10,575,745 B2 | 3/2020 | Solis |
| 10,595,740 B2 | 3/2020 | Hoitink et al. |
| 10,646,692 B2 | 5/2020 | Tegg et al. |
| 10,653,423 B2 | 5/2020 | Starnes |
| 10,835,712 B2 | 11/2020 | Wada |
| 10,842,990 B2 | 11/2020 | de la Rama et al. |
| 10,857,349 B2 | 12/2020 | de la Rama et al. |
| 10,869,992 B2 | 12/2020 | Pai et al. |
| 10,898,685 B2 | 1/2021 | Tegg |
| 10,912,925 B2 | 2/2021 | Houck |
| 10,966,623 B2 | 4/2021 | Wu et al. |
| 10,967,150 B2 | 4/2021 | Helgeson et al. |
| 11,083,400 B2 | 8/2021 | Hoitink et al. |
| 11,160,482 B2 | 11/2021 | Solis |
| 11,272,886 B2 | 3/2022 | Harlev et al. |
| 11,350,987 B2 * | 6/2022 | Pappone ............... A61F 7/12 |

(56) References Cited

U.S. PATENT DOCUMENTS

| | | | |
|---|---|---|---|
| 11,382,690 | B2 | 7/2022 | Smith et al. |
| 11,382,743 | B2 | 7/2022 | Marchand et al. |
| 11,383,078 | B2 | 7/2022 | de la Rama et al. |
| 11,419,673 | B2 | 8/2022 | Kauphusman et al. |
| 11,446,471 | B2 | 9/2022 | Grunewald |
| 11,478,299 | B2 | 10/2022 | Webster et al. |
| 11,491,311 | B2 | 11/2022 | Selkee |
| 11,511,078 | B2 | 11/2022 | Gonzalez |
| 11,523,748 | B2 | 12/2022 | Esguerra Wilczynski et al. |
| 11,583,334 | B2 | 2/2023 | Caples et al. |
| 11,617,616 | B2 | 4/2023 | Clark et al. |
| 11,617,861 | B2 | 4/2023 | Pai et al. |
| 11,622,806 | B2 | 4/2023 | Romoscanu |
| 11,628,009 | B2 | 4/2023 | Aujla |
| 11,857,250 | B2 | 1/2024 | Corvi et al. |
| 11,938,316 | B2 | 3/2024 | Feler et al. |
| 2002/0165484 | A1 | 11/2002 | Bowe et al. |
| 2005/0159741 | A1 | 7/2005 | Paul et al. |
| 2007/0083193 | A1 | 4/2007 | Werneth et al. |
| 2007/0179385 | A1 | 8/2007 | Cho et al. |
| 2009/0054892 | A1 | 2/2009 | Rioux et al. |
| 2009/0137916 | A1 | 5/2009 | Maison-blanche et al. |
| 2009/0198300 | A1 | 8/2009 | Zhang et al. |
| 2010/0137859 | A1* | 6/2010 | Wang ................. A61B 18/1492 606/41 |
| 2011/0118598 | A1 | 5/2011 | Gertner |
| 2011/0118726 | A1 | 5/2011 | de la Rama et al. |
| 2012/0271302 | A1 | 10/2012 | Behl et al. |
| 2012/0296232 | A1 | 11/2012 | Ng |
| 2013/0012938 | A1 | 1/2013 | Asirvatham et al. |
| 2013/0253504 | A1 | 9/2013 | Fang |
| 2013/0274582 | A1 | 10/2013 | Afonso et al. |
| 2014/0005706 | A1 | 1/2014 | Gelfand et al. |
| 2014/0100639 | A1 | 4/2014 | Lee et al. |
| 2014/0200639 | A1 | 7/2014 | de la Rama |
| 2014/0269602 | A1 | 9/2014 | Kawagishi |
| 2014/0296846 | A1 | 10/2014 | Huszar et al. |
| 2014/0296902 | A1 | 10/2014 | Huszar et al. |
| 2014/0316496 | A1 | 10/2014 | Masson et al. |
| 2014/0336636 | A1 | 11/2014 | Huszar et al. |
| 2014/0350564 | A1 | 11/2014 | Huszar et al. |
| 2015/0001191 | A1 | 1/2015 | Lee et al. |
| 2015/0105645 | A1 | 4/2015 | Subramaniam et al. |
| 2015/0119911 | A1 | 4/2015 | Mckenzie |
| 2015/0141785 | A1 | 5/2015 | Hayam et al. |
| 2015/0159741 | A1 | 6/2015 | Versteyhe et al. |
| 2015/0351652 | A1 | 12/2015 | Marecki et al. |
| 2016/0143588 | A1 | 5/2016 | Hoitink et al. |
| 2016/0213423 | A1 | 7/2016 | Kauphusman et al. |
| 2016/0213916 | A1 | 7/2016 | de la Rama |
| 2016/0317094 | A1 | 11/2016 | Byrd et al. |
| 2016/0374582 | A1 | 12/2016 | Wu et al. |
| 2017/0042449 | A1 | 2/2017 | Deno et al. |
| 2017/0049348 | A1 | 2/2017 | Deno et al. |
| 2018/0050190 | A1 | 2/2018 | Masson |
| 2018/0070845 | A1 | 3/2018 | Hoitink et al. |
| 2018/0303361 | A1 | 10/2018 | Wu et al. |
| 2020/0054391 | A1 | 2/2020 | Litscher et al. |
| 2020/0138378 | A1 | 5/2020 | de la Rama et al. |
| 2020/0155021 | A1 | 5/2020 | Wu et al. |
| 2020/0229727 | A1 | 7/2020 | Hoitink et al. |
| 2020/0253496 | A1 | 8/2020 | Deno et al. |
| 2020/0405166 | A1 | 12/2020 | Wu et al. |
| 2021/0145342 | A1 | 5/2021 | Wang |
| 2021/0187246 | A1 | 6/2021 | Houck |
| 2021/0268234 | A1 | 9/2021 | Helgeson et al. |
| 2021/0361216 | A1 | 11/2021 | Hoitink et al. |
| 2022/0023594 | A1 | 1/2022 | Pai |
| 2022/0054066 | A1 | 2/2022 | Solis |
| 2022/0273913 | A1 | 9/2022 | Worley et al. |
| 2022/0370792 | A1 | 11/2022 | De La Rama et al. |
| 2022/0387012 | A1 | 12/2022 | Nunan |
| 2023/0084626 | A1 | 3/2023 | Grunewald |
| 2023/0114222 | A1 | 4/2023 | Esguerra Wilczynski et al. |
| 2023/0190369 | A1 | 6/2023 | Caples et al. |
| 2023/0329784 | A1 | 10/2023 | Stewart et al. |
| 2024/0081905 | A1 | 3/2024 | Corvi et al. |

FOREIGN PATENT DOCUMENTS

| | | |
|---|---|---|
| CN | 102164555 A | 8/2011 |
| CN | 102302364 A | 1/2012 |
| CN | 102892368 A | 1/2013 |
| CN | 103718191 A | 4/2014 |
| CN | 101927053 B | 1/2015 |
| CN | 103157168 B | 4/2015 |
| CN | 105960201 A | 9/2016 |
| CN | 104434083 B | 4/2019 |
| CN | 104968261 B | 5/2019 |
| CN | 105592778 B | 7/2019 |
| CN | 105960200 B | 8/2019 |
| CN | 105451680 B | 10/2019 |
| CN | 105960201 B | 3/2020 |
| CN | 107529958 B | 7/2021 |
| CN | 110559544 B | 9/2021 |
| CN | 105615994 B | 10/2021 |
| CN | 110547865 B | 10/2022 |
| CN | 115444549 A | 12/2022 |
| CN | 112704546 B | 3/2024 |
| EP | 0680284 A1 | 11/1995 |
| EP | 0779059 A1 | 6/1997 |
| EP | 0889744 B1 | 1/2004 |
| EP | 1254641 B1 | 11/2008 |
| EP | 1690564 B1 | 4/2009 |
| EP | 1723981 B1 | 8/2010 |
| EP | 2135634 B1 | 10/2011 |
| EP | 2018203 B1 | 6/2012 |
| EP | 1814450 B1 | 1/2013 |
| EP | 2269532 B1 | 3/2013 |
| EP | 2664295 A1 | 11/2013 |
| EP | 2604306 B1 | 1/2014 |
| EP | 2732843 A1 | 5/2014 |
| EP | 2747680 A2 | 7/2014 |
| EP | 2752153 A1 | 7/2014 |
| EP | 2907462 A1 | 8/2015 |
| EP | 2915555 A1 | 9/2015 |
| EP | 3023052 A1 | 5/2016 |
| EP | 1968679 B1 | 9/2016 |
| EP | 2241279 B1 | 9/2016 |
| EP | 2796103 B1 | 2/2017 |
| EP | 2792322 B1 | 10/2017 |
| EP | 2792323 B1 | 10/2017 |
| EP | 3115076 A4 | 10/2017 |
| EP | 3117863 A4 | 10/2017 |
| EP | 3030182 B1 | 1/2018 |
| EP | 3111872 B1 | 4/2018 |
| EP | 3057488 B1 | 5/2018 |
| EP | 2848226 B1 | 7/2018 |
| EP | 3391928 A1 | 10/2018 |
| EP | 3122276 B1 | 11/2018 |
| EP | 3398549 A1 | 11/2018 |
| EP | 1759668 B1 | 12/2018 |
| EP | 3037122 B1 | 12/2018 |
| EP | 2234537 B1 | 1/2019 |
| EP | 2569040 B1 | 2/2019 |
| EP | 3023052 B1 | 3/2019 |
| EP | 3073908 B1 | 4/2019 |
| EP | 3466363 A1 | 4/2019 |
| EP | 2550989 B1 | 6/2019 |
| EP | 3527125 A1 | 8/2019 |
| EP | 3434218 B1 | 2/2020 |
| EP | 2908723 B1 | 3/2020 |
| EP | 3335658 B1 | 4/2020 |
| EP | 3073907 B1 | 6/2020 |
| EP | 3708104 A1 | 9/2020 |
| EP | 3721796 A1 | 10/2020 |
| EP | 3738508 A1 | 11/2020 |
| EP | 3738509 A1 | 11/2020 |
| EP | 3679861 B1 | 2/2021 |
| EP | 2155301 B1 | 4/2021 |
| EP | 2809254 B1 | 6/2021 |
| EP | 4039215 A1 | 8/2022 |
| EP | 3363397 B1 | 9/2022 |

(56) References Cited

FOREIGN PATENT DOCUMENTS

| | | | |
|---|---|---|---|
| EP | 4101372 | A1 | 12/2022 |
| EP | 2844193 | B1 | 1/2023 |
| EP | 3100696 | B1 | 1/2023 |
| EP | 3166524 | B1 | 1/2023 |
| EP | 3115076 | B1 | 3/2023 |
| EP | 2803329 | B1 | 6/2023 |
| EP | 3015064 | B1 | 6/2023 |
| EP | 3398549 | B1 | 6/2023 |
| EP | 4190232 | A1 | 6/2023 |
| EP | 2816966 | B1 | 10/2023 |
| EP | 3113671 | B1 | 10/2023 |
| EP | 3738509 | B1 | 10/2023 |
| EP | 3209234 | B1 | 11/2023 |
| EP | 3527125 | B1 | 11/2023 |
| EP | 3721796 | B1 | 11/2023 |
| EP | 4233699 | A3 | 11/2023 |
| EP | 4272631 | A2 | 11/2023 |
| EP | 4298995 | A2 | 1/2024 |
| EP | 3738508 | B1 | 2/2024 |
| JP | 2010510826 | A | 4/2010 |
| JP | 4545384 | B2 | 7/2010 |
| JP | 4887810 | B2 | 2/2012 |
| JP | 4940332 | B2 | 3/2012 |
| JP | 2012055602 | A | 3/2012 |
| JP | 2012508083 | A | 4/2012 |
| JP | 2012200509 | A | 10/2012 |
| JP | 5154031 | B2 | 2/2013 |
| JP | 5193190 | B2 | 5/2013 |
| JP | 5372314 | B2 | 12/2013 |
| JP | 2014014713 | A | 1/2014 |
| JP | 5550150 | B2 | 5/2014 |
| JP | 5762697 | B2 | 6/2015 |
| JP | 5856712 | B2 | 2/2016 |
| JP | 5908270 | B2 | 4/2016 |
| JP | 5944331 | B2 | 7/2016 |
| JP | 6050522 | B2 | 12/2016 |
| JP | 6059737 | B2 | 12/2016 |
| JP | 2017051211 | A | 3/2017 |
| JP | 6246742 | B2 | 12/2017 |
| JP | 6342524 | B2 | 6/2018 |
| JP | 6434495 | B2 | 12/2018 |
| JP | 6445509 | B2 | 12/2018 |
| JP | 6466114 | B2 | 2/2019 |
| JP | 6479005 | B2 | 2/2019 |
| JP | 6515084 | B2 | 5/2019 |
| JP | 6655655 | B2 | 2/2020 |
| JP | 6746734 | B2 | 8/2020 |
| JP | 6843502 | B2 | 3/2021 |
| JP | 6926306 | B2 | 8/2021 |
| JP | 6980386 | B2 | 11/2021 |
| JP | 7101228 | B2 | 7/2022 |
| WO | 9843530 | A1 | 10/1998 |
| WO | 0168178 | A1 | 9/2001 |
| WO | 2008065609 | A1 | 6/2008 |
| WO | 2008091197 | A1 | 7/2008 |
| WO | 2010056771 | A1 | 5/2010 |
| WO | 2014113612 | A1 | 7/2014 |
| WO | 2015057521 | A1 | 4/2015 |
| WO | 2015095577 | A1 | 6/2015 |
| WO | 2015130824 | A1 | 9/2015 |
| WO | 2016001015 | A1 | 1/2016 |

OTHER PUBLICATIONS

Dumaine et al., "Ionic Mechanisms Responsible for the Electrocardiogramanotype of the Brugada Syndrome are Temperature Dependent", Circulation Research, vol. 85, No. 9, Oct. 29, 1999, pp. 803-809.

Keller et al., "Brugada Syndrome and Fever: Genetic and Molecular Characterization of Patients Carrying SCN5A Mutations", Cardiovascular Research, vol. 67, No. 3, Aug. 15, 2005, pp. 510-519.

Mizusawa et al., "Brugada Syndrome", Circulation: Arrhythmia and Electrophysiology, vol. 5, No. 3, Jun. 2012, pp. 606-616.

Morita et al., "Temperature Modulation of Ventricular Arrhythmogenicity in a Canine Tissue Model of Brugada Syndrome", Heart Rhythm, vol. 4, No. 2, Feb. 2007, pp. 188-197.

Nademanee et al., "Prevention of Ventricular Fibrillation Episodes in Brugada Syndrome by Catheter Ablation Over the Anterior Right Ventricular Outflow Tract Epicardium", Circulation, vol. 123, No. 12, Mar. 29, 2011, pp. 1270-1279.

Shah et al., "Regional Substrate Ablation Abolishes Brugada Syndrome", Journal of Cardiovascular Electrophysiology, vol. 22, No. 11, Nov. 2011, pp. 1290-1291.

Wolpert et al., "Intravenous Drug Challenge Using Flecainide and Ajmaline in Patients with Brugada Syndrome", Heart Rhythm, vol. 2, No. 23, Mar. 2005, pp. 254-260.

* cited by examiner

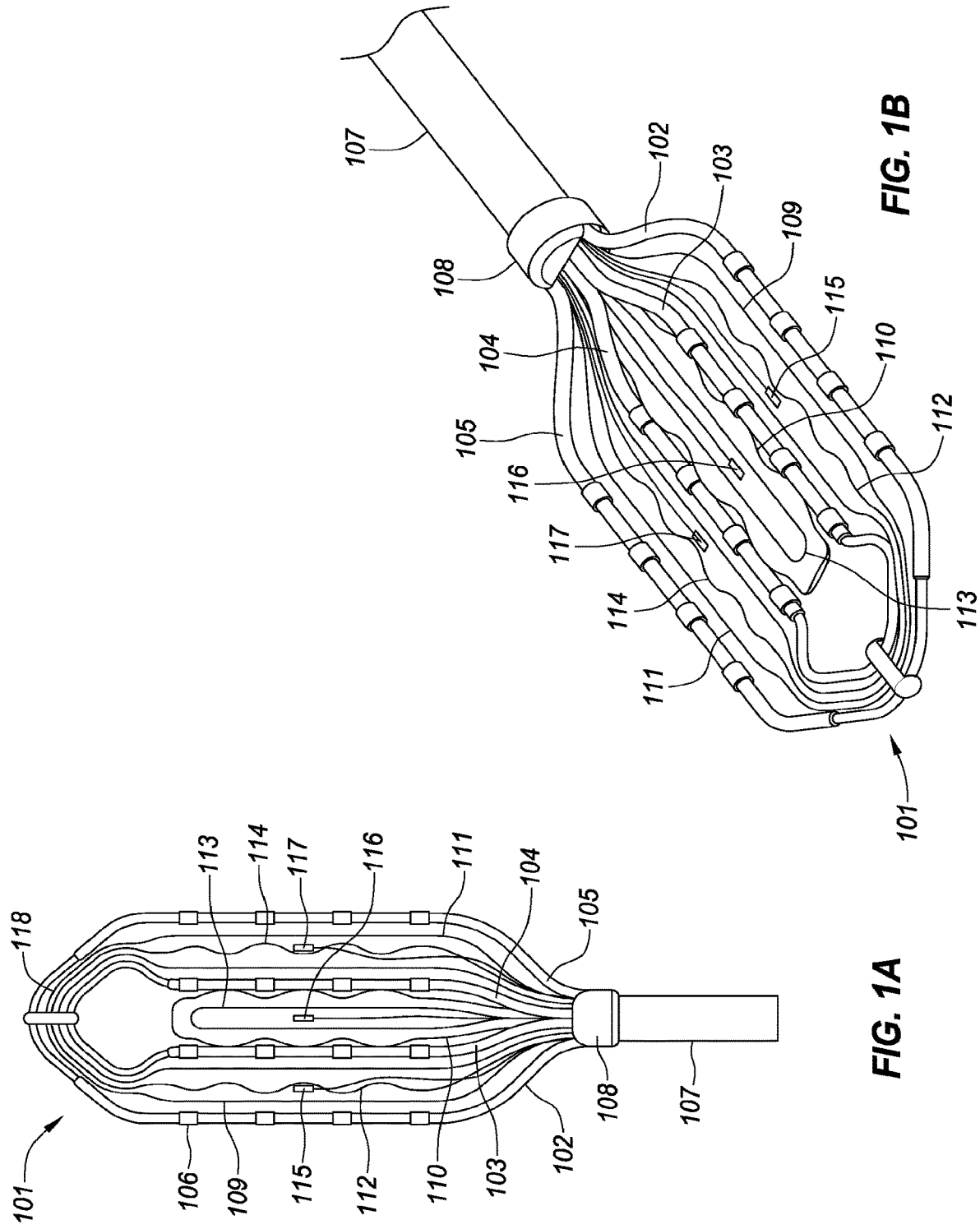

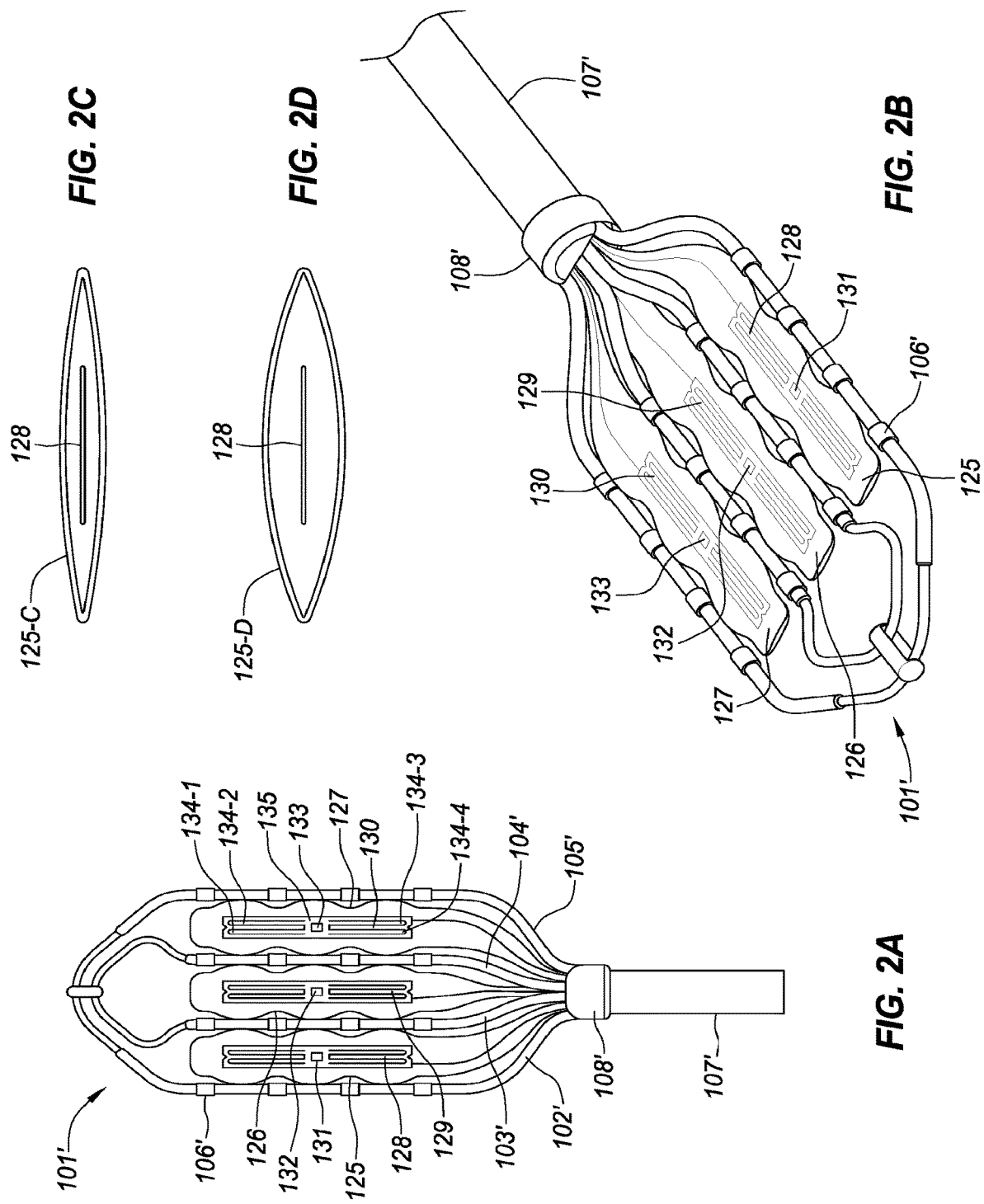

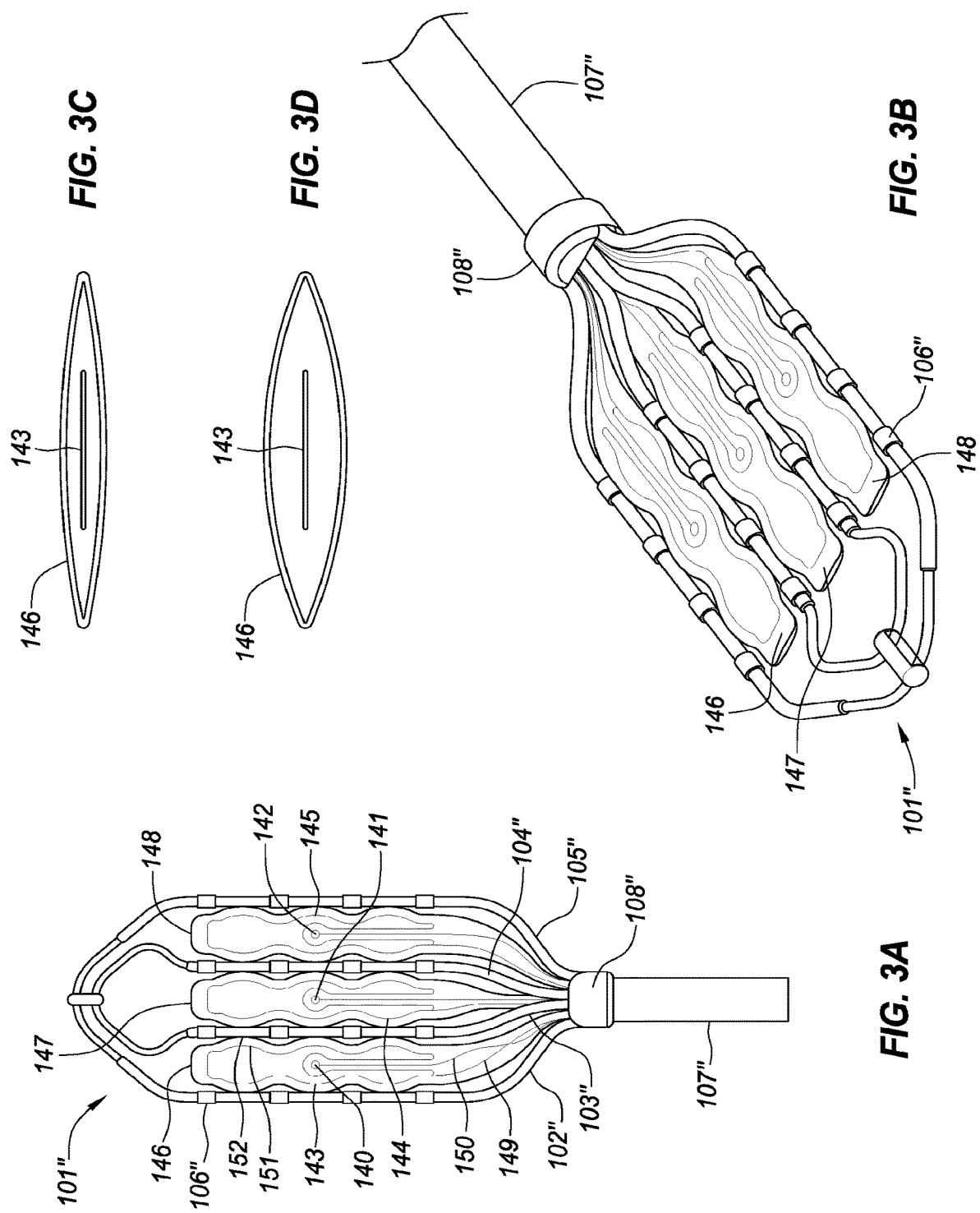

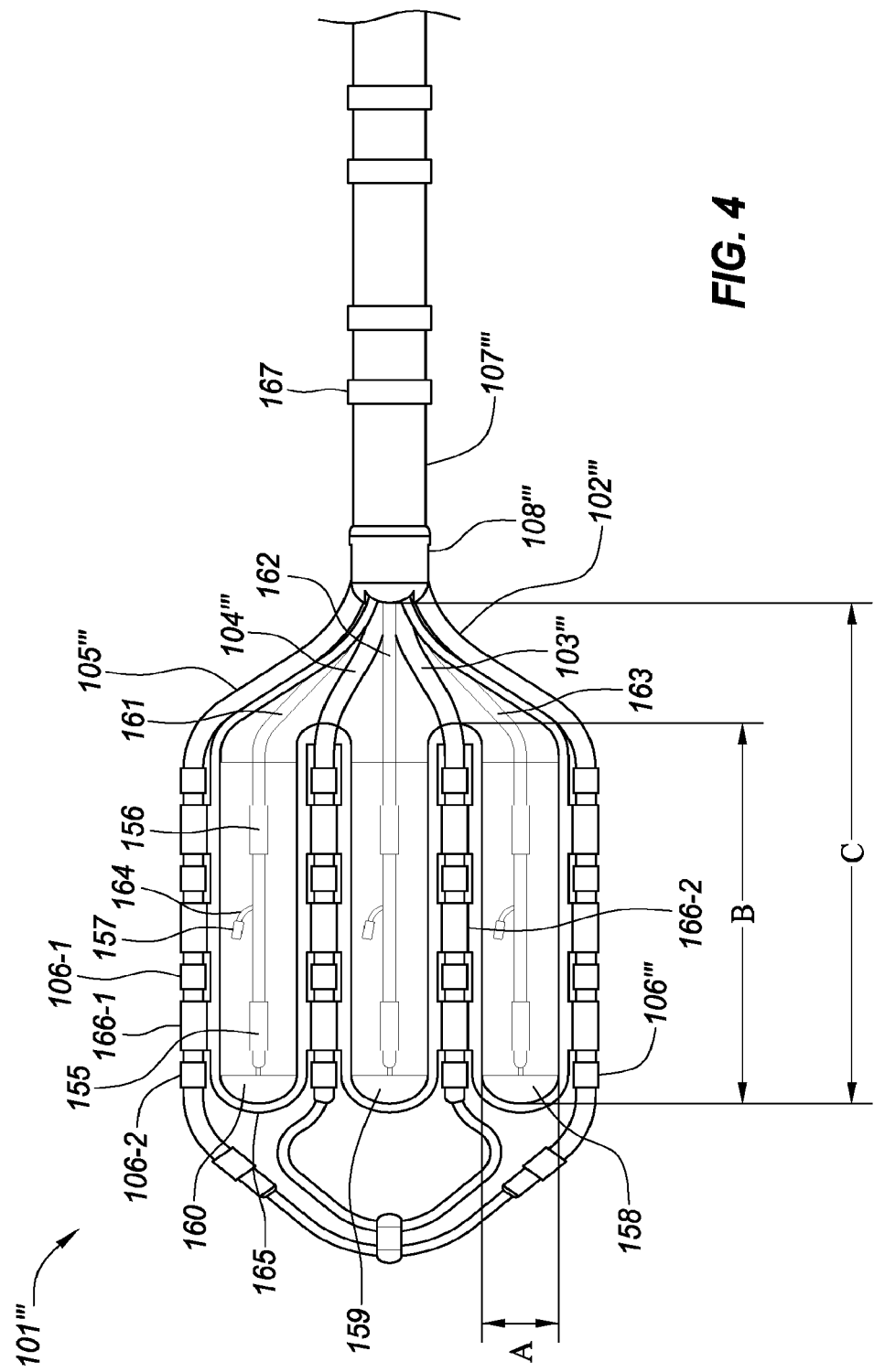

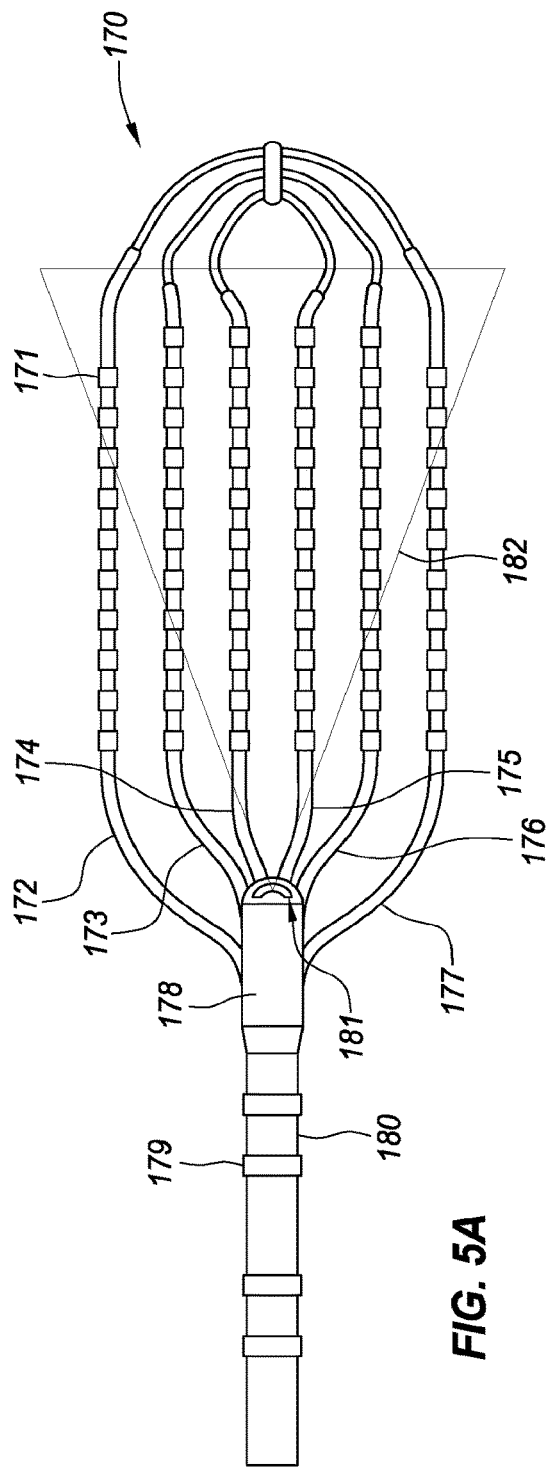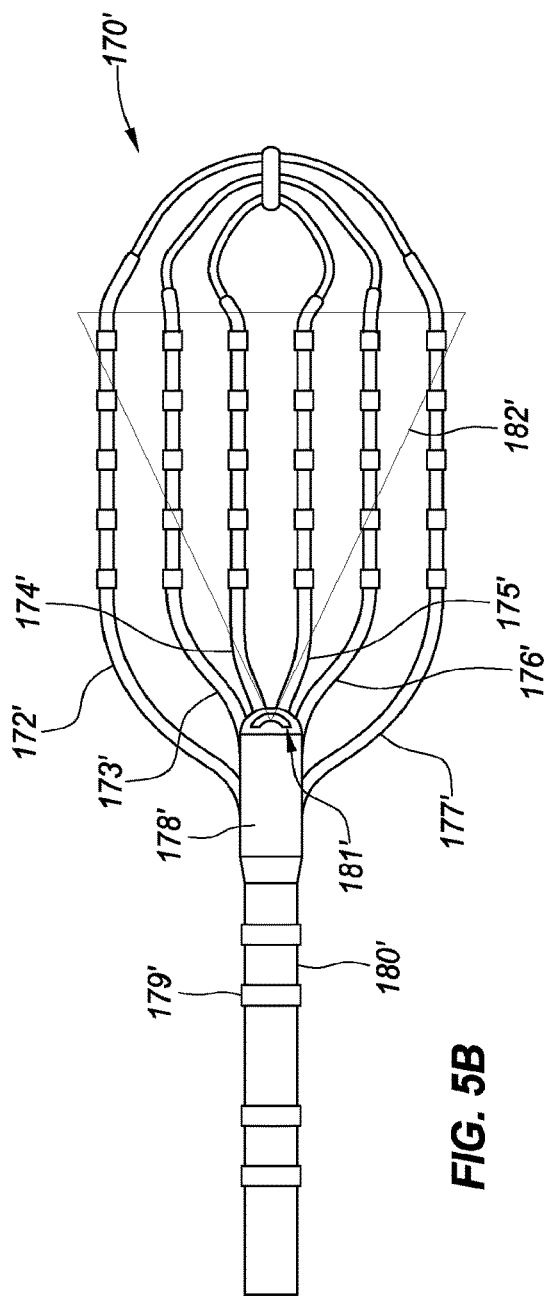
FIG. 5A
FIG. 5B

THERMAL MAPPING CATHETER

CROSS-REFERENCE TO RELATED APPLICATION

This application is a continuation of U.S. application Ser. No. 15/546,991, filed 27 Jul. 2017 (the '991 application, now U.S. Pat. No. 11,350,987), which is the national stage of international application no. PCT/US2016/015449, filed 28 Jan. 2016 (the '449 application), and published under International publication no. WO 2016/123390 on 4 Aug. 2016. This application claims priority to U.S. provisional patent application No. 62/108,945 filed 28 Jan. 2015. The '991 application, the '449 application and the '945 application are all hereby incorporated by reference in their entirety as though fully set forth herein.

a. Field of the Disclosure

This disclosure relates to a thermal mapping catheter.

b. Background Art

Catheters have been used for cardiac medical procedures for many years. Catheters can be used, for example, to diagnose and treat cardiac arrhythmias, while positioned at a specific location within a body that is otherwise inaccessible without a more invasive procedure.

Conventional mapping catheters may include, for example, a plurality of adjacent ring electrodes encircling the longitudinal axis of the catheter and constructed from platinum or some other metal. These ring electrodes are relatively rigid. Similarly, conventional ablation catheters may comprise a relatively rigid tip electrode for delivering therapy (e.g., delivering RF ablation energy) and may also include a plurality of adjacent ring electrodes. It can be difficult to maintain good electrical contact with cardiac tissue when using these conventional catheters and their relatively rigid (or nonconforming), metallic electrodes, especially when sharp gradients and undulations are present.

Whether mapping or forming lesions in a heart, the beating of the heart, especially if erratic or irregular, complicates matters, making it difficult to keep adequate contact between electrodes and tissue for a sufficient length of time. These problems are exacerbated on contoured or trabeculated surfaces. If the contact between the electrodes and the tissue cannot be sufficiently maintained, quality lesions or accurate mapping are unlikely to result.

The foregoing discussion is intended only to illustrate the present field and should not be taken as a disavowal of claim scope.

BRIEF SUMMARY

Various embodiments of the present disclosure can include a catheter. The catheter can comprise a catheter shaft including a proximal end and a distal end. A flexible framework can be connected to the distal end of the catheter shaft, wherein the flexible framework includes a plurality of heating electrodes and a temperature sensor. The plurality of heating electrodes can be configured to be heated to a first temperature, the first temperature being lower than which radio frequency ablation is performed. The plurality of heating electrodes can be configured to be heated to a second temperature, the second temperature being a temperature at which radio frequency ablation is performed.

Various embodiments of the present disclosure can include a catheter. The catheter can comprise a catheter shaft including a proximal end and a distal end. A flexible framework can be connected to the distal end of the catheter shaft. The flexible framework can include a plurality of electrodes disposed thereon. A fluid sac can be connected to the flexible framework. The fluid sac can include a heater and can be configured to be filled with a fluid.

Various embodiments of the present disclosure can include a method for thermal mapping and ablation. The method can comprise causing a plurality of heating electrodes disposed on a flexible framework to be heated to a first temperature lower than which radio frequency ablation is performed for a defined time. The method can comprise receiving a plurality of mapping signals from a plurality of mapping electrodes disposed on the flexible framework during a portion of the defined time. The method can comprise determining whether any of the plurality of mapping signals exhibit a particular electrical pattern. The method can comprise causing one or more of the plurality of heating electrodes disposed on the flexible framework to be heated to a second temperature at which radio frequency ablation is performed, based on the determination.

Various embodiments of the present disclosure can include a catheter. The catheter can comprise a catheter shaft including a proximal end and a distal end. A flexible framework can be connected to the distal end of the catheter shaft, wherein the flexible framework includes a plurality of electrodes disposed thereon. An irrigation channel can extend through the catheter shaft and an irrigation port can be disposed at the distal end of the catheter shaft and can be in fluid communication with the irrigation channel. The catheter can be configured to expel heated fluid from the irrigation port and monitor mapping signals produced by a tissue via the plurality of electrodes disposed on the flexible framework.

BRIEF DESCRIPTION OF THE DRAWINGS

FIG. 1A is a top view of a thermal mapping catheter, according to various embodiments of the present disclosure.

FIG. 1B is an isometric front, side and top view of the thermal mapping catheter depicted in FIG. 1A, according to various embodiments of the present disclosure.

FIG. 2A is a top view of a second embodiment of a thermal mapping catheter, according to various embodiments of the present disclosure.

FIG. 2B is an isometric front, side and top view of the second embodiment of the thermal mapping catheter depicted in FIG. 2A, according to various embodiments of the present disclosure.

FIG. 2C is a cross-sectional front view of a fluid sac of the second embodiment of the thermal mapping catheter, as shown in FIG. 2A, according to various embodiments of the present disclosure.

FIG. 2D is a cross-sectional front view of a fluid sac of the second embodiment of the thermal mapping catheter, as shown in FIG. 2A, in an expanded state, according to various embodiments of the present disclosure.

FIG. 3A is a top view of a third embodiment of a thermal mapping catheter, according to various embodiments of the present disclosure.

FIG. 3B is an isometric front, side and top view of the third embodiment of the thermal mapping catheter depicted in FIG. 3A, according to various embodiments of the present disclosure.

FIG. 3C is a cross-sectional front view of a fluid sac of the third embodiment of the thermal mapping catheter, as shown in FIG. 3A, according to various embodiments of the present disclosure.

FIG. 3D is a cross-sectional front view of a fluid sac of the third embodiment of the thermal mapping catheter, as shown in FIG. 3A, in an expanded state, according to various embodiments of the present disclosure.

FIG. 4 is a top view of a fourth embodiment of a thermal mapping catheter, according to various embodiments of the present disclosure.

FIG. 5A is a top view of a fifth embodiment of a thermal mapping catheter with a first number of electrodes, according to various embodiments of the present disclosure.

FIG. 5B is a top view of a fifth embodiment of the thermal mapping catheter with a second number of electrodes, according to various embodiments of the present disclosure.

DETAILED DESCRIPTION

Figure 5C:
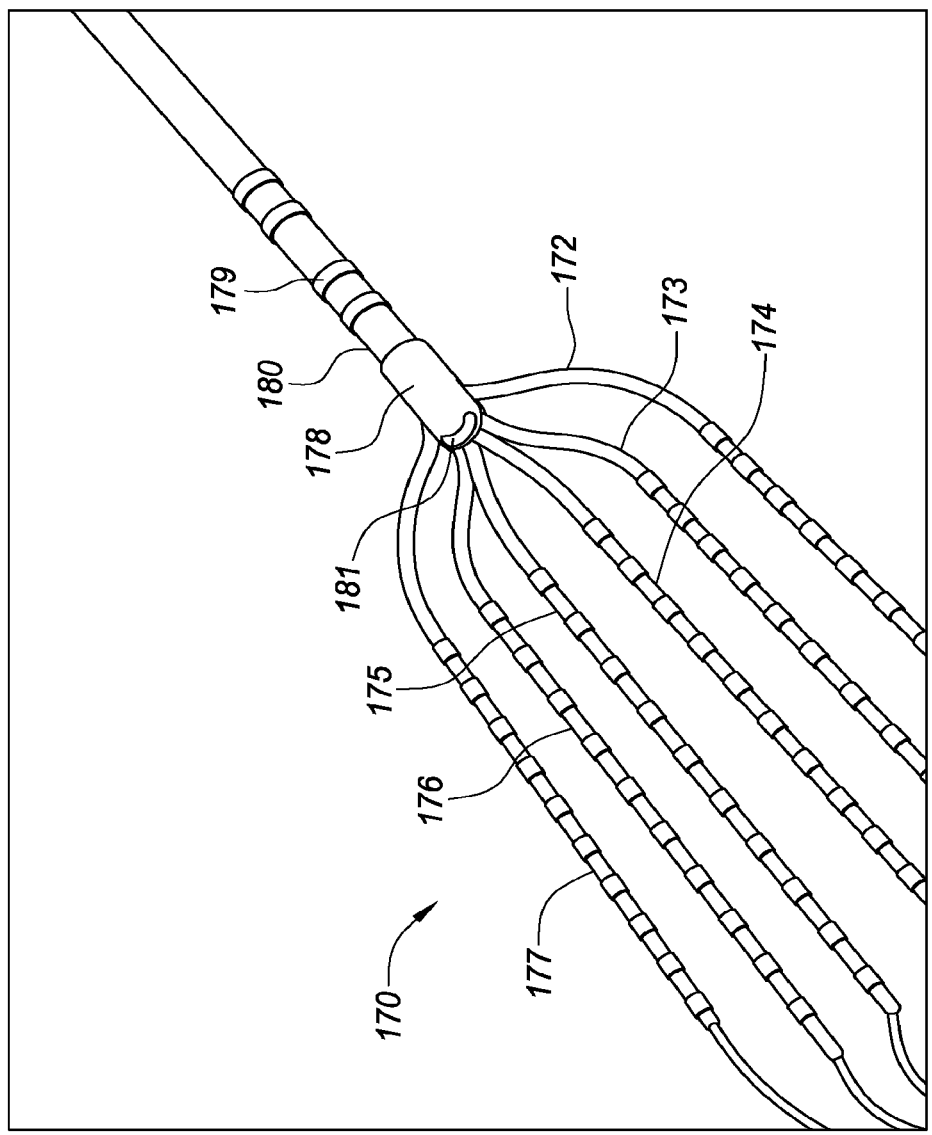
FIG. 5C is an isometric front, side and top view of the fifth embodiment of the thermal mapping catheter shown in FIG. 5B, according to various embodiments of the present disclosure.

The contents of International Application No. PCT/US2014/011940 entitled Flexible High-Density Mapping Catheter Tips and Flexible Ablation Catheter Tips with Onboard High-Density Mapping Electrodes is hereby incorporated by reference.

In an example, some syndromes can cause ventricular fibrillation, which can lead to health risks and/or death. For instance, syndromes such as Brugada syndrome (BrS) can have a heterogeneous genetic basis with more than 15 different genes involving different channels being described as responsible for a Brugada electrocardiogram (ECG) pattern expression. SCN5A mutations are the most commonly found mutations in 15-30% of patients with BrS, an autosomal-dominant inherited arrhythmic disorder characterized by ST elevation with a successive negative T wave in the right precordial leads with an absence of gross structural abnormalities. Patients with BrS are at risk for sudden cardiac death due to ventricular fibrillation. The SCN5A mutations in BrS are also associated with incomplete penetrance and variable expressivity, and many patients with the mutation never develop symptoms of the disease. Hence, there is great controversy and difficulty over which patients are likely to develop a life threatening arrhythmia and who may need preventive therapy.

Diagnosis of BrS requires a high level of suspicion due to a resting ECG that is frequently borderline intermittently normal or frankly normal. Genetic testing is not sensitive and may yield results that are difficult to interpret. Pharmacologic challenge testing with intravenous administration of sodium channel blockers such as flecainide, ajmaline, pilsidcainide, and procainamide have been used to unmask the ECG pattern in patients with BrS by provoking ST-segment elevation. However studies have shown that these drugs are far less than 100% sensitive and specific for BrS.

Fever can play a role for ventricular arrhythmias in patients with sodium channel disorders. Although the exact mechanism remains elusive, one explanation is that mutations associated with BrS changes the temperature sensitivity of fast inactivation of the sodium channel.

According to embodiments of the present disclosure, in an example, a portion of the heart can be warmed to mimic a rise in body temperature to unmask the Brugada pattern. Some embodiments of the present disclosure can include a thermal mapping catheter that can be configured to warm a portion of the heart and collect electrical signals produced by the heart. Some embodiments of the present disclosure can include a thermal mapping catheter that can be configured to acquire mapping points associated with locations where ablation is to be performed, based on the collection of the electrical signals. Some embodiments of the present disclosure can include a thermal mapping catheter that is configured to ablate tissue (e.g., cardiac tissue).

Some embodiments of the present disclosure can be used to increase a temperature of cardiac tissue (e.g., epicardial tissue). In some embodiments, the temperature of the cardiac tissue can be increased after a sodium blocker infusion (e.g., flecainide, ajmaline, pilsidcainide, procainamide infusion) has been performed. A detailed electroanatomical voltage map (e.g., epicardial voltage map) can be created using embodiments of the present disclosure to collect electrical signals from the tissue, which can then be assembled into the electroanatomical voltage map.

FIG. 1A is a top view of a thermal mapping catheter 101 and FIG. 1B is an isometric front, side and top view of the thermal mapping catheter 101, according to various embodiments of the present disclosure. In some embodiments, the thermal mapping catheter 101 can include a flexible array of microelectrodes. This planar array (or 'paddle' configuration) of microelectrodes comprises four side-by-side, longitudinally-extending arms 102, 103, 104, 105, which can form a flexible framework on which ring electrodes 106 are carried. The four ring-electrode-carrier arms comprise a first outboard arm 102, a second outboard arm 105, a first inboard arm 103, and a second inboard arm 104. These arms can be laterally separated from each other. Each of the four arms can carry a plurality of ring electrodes 106. For example, each of the four arms can carry ring electrodes 106 spaced along a length of each of the four arms. Although the paddle catheter depicted in FIGS. 1A and 1B include four arms, the paddle could comprise more or fewer arms.

In some embodiments, the thermal mapping catheter 101 can include a catheter shaft 107. The catheter shaft 107 can include a proximal end and a distal end. The distal end can include a connector 108, which can couple the distal end of the catheter shaft 107 to a proximal end of the planar array (e.g., flexible framework). The catheter shaft 107 can be made of a flexible material, such that it can be threaded through a tortuous vasculature of a patient.

In some embodiments, fluid sacs can be disposed between the first outboard arm 102 and the first inboard arm 103, between the first inboard arm 103 and the second inboard arm 104, and between the second inboard arm 104 and the second outboard arm 105. In an example, the fluid sacs can extend from the proximal end of the planar array to a distal end of the planar array. For instance, a first fluid sac 109 can be disposed between the first outboard arm 102 and the first inboard arm 103, a second fluid sac 110 can be disposed between the first inboard arm 103 and the second inboard arm 102, and a third fluid sac 111 can be disposed between the second inboard arm 104 and the second outboard arm 105. In some embodiments, one or more fluid sacs can be disposed between at least a pair of the longitudinally-extending arms 102, 103, 104, 105.

In some embodiments, the fluid sacs can be formed of a flexible material such as a rubber (e.g., latex) and/or a plastic. Further, the arms (or the understructure of the arms) comprising the paddle structure (or multi-arm, electrode-carrying, flexible framework) at the distal end of the catheter are preferably constructed from a flexible or spring-like material such as Nitinol. The construction (including, for example, the length and/or diameter of the arms and/or length and/or thickness of the fluid sacs) and material of the arms and/or fluid sacs can be adjusted or tailored to be created, for example, desired resiliency, flexibility, foldability, conformability, and stiffness characteristics, including one or more characteristics that may vary from the proximal end of a single arm to the distal end of that arm, or between or among the plurality of arms comprising a single paddle structure. In an example, the thermal mapping catheter 101 can be folded to allow insertion through a vasculature of a patient, in some embodiments. The foldability of the materials from which the materials that the catheter is formed from provide the additional advantage of facilitating insertion of the paddle structure into a delivery catheter or introducer, whether during delivery of the catheter into the body or removal of the catheter from the body at the end of a procedure.

In some embodiments, the fluid sacs can include heaters 112, 113, 114. The heaters 112, 113, 114 can be formed from a conductive flexible wire. In an example, electricity can be supplied to the flexible wire, which can resistively heat the wire. The heat from the heaters 112, 113, 114 can be transferred to the fluid included in the fluid sacs 109, 110, 111. In an example, the fluid can be a saline solution. In some embodiments, each of the fluid sacs 109, 110, 111 can include temperature sensors 115, 116, 117 (e.g., thermocouples). The temperature sensors 115, 116, 117 can be attached to an inside of each of the fluid sacs 109, 110, 111 and can be in fluid communication with the fluid included in each of the fluid sacs 109, 110, 111. The temperature of the fluid can thus be sensed by the temperature sensors 115, 116, 117 and a signal produced by the temperature sensors can be used to control heating of the fluid by the heaters. In some embodiments, the fluid can be heated to a temperature in a range of 50 degrees Celsius to 60 degrees Celsius. However, the fluid can be heated to a temperature less than 50 degrees Celsius and/or greater than a temperature of 60 degrees Celsius in some embodiments. In some embodiments, the fluid can be heated to a temperature of 40 degrees Celsius to 60 degrees Celsius. In some embodiments, the fluid can be heated to a temperature of 40 degrees Celsius to 48 degrees Celsius. In some embodiments, the fluid can be heated to a temperature in a range of 35 degrees Celsius to 65 degrees Celsius. In some embodiments, the fluid can be heated to a temperature in a range from 38 degrees Celsius to 42 degrees Celsius. Upon contact between the fluid sacs 109, 110, 111 and the tissue, the tissue can be warmed, which can help unmask the Brugada pattern. In some embodiments, the tissue can be warmed via the fluid sacs 109, 110, 111 to a temperature in a range from 38 degrees Celsius to 42 degrees Celsius, which can cause the tissue to exhibit an ECG pattern recognizable as the Brugada pattern. However, in some embodiments, the tissue can be warmed to a temperature greater than 42 degrees Celsius. For example, in some embodiments, the tissue can be heated to a temperature in a range from 38 degrees Celsius to 45 degrees Celsius, 38 degrees Celsius to 50 degrees Celsius, 42 degrees Celsius to 48 degrees Celsius, and/or 42 degrees Celsius to 50 degrees Celsius. In some embodiments, when heating the tissue to an upper range within the above and below noted ranges to cause the tissue to exhibit the ECG pattern recognizable as the Brugada pattern, the tissue can be momentarily heated to that temperature to avoid damage to the tissue.

Electrical signals can be collected from the tissue via the electrodes 106. The tissue can then also be ablated with the electrodes 106, in some embodiments, by heating the electrodes to a temperature associated with the performance of ablation, as discussed herein. In some embodiments, the heaters 112, 113, 114, the temperature sensors 115, 116, 117, and/or electrodes 106 can be controlled via a system and/or computing device discussed in relation to FIGS. 9A and 9B.

In some embodiments, the fluid sacs 109, 110, 111 can be in fluid communication with one or more supply tubes that extend through the catheter shaft. In an example, a proximal end of each of the fluid sacs 109, 110, 111 can be in fluid communication with the one or more supply tubes. The thermal mapping catheter 101 can include a fluid pump, for example, at a proximal end of the thermal mapping catheter 101 (e.g., in a catheter handle, proximal to the catheter handle) that is configured to pump fluid through the one or more supply tubes into the fluid sacs 109, 110, 111. The fluid can be static or dynamic. For example, the fluid that the fluid sacs 109, 110, 111 are filled with can remain stationary and/or or can be circulated through each of the fluid sacs 109, 110, 111.

In an example, the fluid sacs 109, 111 can be in fluid communication with one another. For example, the fluid sacs 109, 111 can be in fluid communication via a fluid conduit 118. Fluid can be fed into one of the fluid sacs 109, 111, and returned through the other fluid sac. For example, fluid can be fed into fluid sac 109 and returned through fluid sac 111. Alternatively, fluid can be fed into fluid sac Ill and returned through fluid sac 109.

In some embodiments, the fluid sacs 109, 110, 111 can be connected to the arms 102, 103, 104, 105. For example, the first fluid sac 109 can be connected to the first outboard arm 102 and the first inboard arm 103, the second fluid sac 110 can be connected to the first inboard arm 103 and the second inboard arm 104, and the third fluid sac can be connected to the second inboard arm 104 and the second outboard arm 105. In an example, each of the fluid sacs 109, 110, 111 can be connected to one another via connection tabs, as further illustrated in FIG. 4.

In some embodiments, a width of the fluid sacs 109, 110, 111 can be configured to fit between each of the arms. For example, a width of the fluid sac 109 can be configured to fit between the first outboard arm 102 and the first inboard arm 103; a width of the second fluid sac 110 can be configured to fit between the first inboard arm 103 and the second inboard arm 104; and a width of the third fluid sac 111 can be configured to fit between the second inboard arm 104 and the second outboard arm 111. In some embodiments, as further discussed in relation to FIGS. 3C and 3D, a height of the fluid sacs 109, 110, 111 in a filled state can be configured to be less than a height of each of the respective arms 102, 103, 104, 105.

FIG. 2A is a top view of a second embodiment of a thermal mapping catheter 101'. The thermal mapping catheter 101' can include longitudinally extending arms 102', 103', 104', 105', which can form the flexible framework on which ring electrodes 106' are carried. The thermal mapping catheter 101 can also include the catheter shaft 107' and the connector 108'. The thermal mapping catheter 101' can include fluid sacs 125, 126, 127, as discussed in relation to FIG. 1A. In some embodiments, the fluid sacs 125, 126, 127 can be individual fluid sacs (i.e., not connected to one another). For example, the fluid sacs 125, 127 can be separate from one another and not in fluid communication with one another via the fluid conduit 118, as discussed in relation to FIG. 1A.

In some embodiments, the thermal mapping catheter 101' can include flexible circuits 128, 129, 130, which can serve as heating elements to heat the fluid. In some embodiments, the flexible circuits can include temperatures sensors 131, 132, 133, as discussed in relation to FIG. 1A. The flexible circuits can be folded in some embodiments. In an example, as the thermal mapping catheter 101' is collapsed and the longitudinally-extending arms 102', 103', 104', 105' move closer to one another, the flexible circuits can be folded longitudinally, such that a lateral width of the folded circuits is reduced. For instance, the flexible circuits 128, 129, 130 can be folded in half lengthwise, along a longitudinal axis of each respective flexible circuit 128, 129, 130, such that a width of each one of the flexible circuits 128, 129, 130 is decreased when the thermal mapping catheter 101' is in an undeployed state.

In some embodiments, as depicted in FIG. 2A with respect to flexible circuit 130, the flexible circuit 130 can include one or more longitudinally and distally extending heater elements (e.g., distal heater elements 134-1, 134-2) and one or more longitudinally and proximally extending heater elements (e.g., proximal heater elements 134-3, 134-4) that extend from a heater element bus 135. In some embodiments, the distal heater elements 134-1, 134-2 and the proximal heater elements 134-3, 134-4 can be electrically coupled via the heater bus 135. The heater elements 134-1, 134-2, 134-3, 134-4 can be formed on a substrate, in some embodiments, such as a printed circuit board (PCB) and can be electrically coupled to a power source via one or more leads electrically coupled to the flexible circuit that extend through the catheter shaft 107'. Although flexible heater circuit 130 is discussed, the flexible circuits 128, 129 can include features similar to those discussed in relation to flexible heater circuit 130.

As previously discussed, in some embodiments, the fluid can be heated to a temperature in a range of 50 degrees Celsius to 60 degrees Celsius. However, the fluid can be heated to a temperature less than 50 degrees Celsius and/or greater than a temperature of 60 degrees Celsius. In some embodiments, the fluid can be heated to a temperature of 40 degrees Celsius to 60 degrees Celsius. In some embodiments, the fluid can be heated to a temperature of 40 degrees Celsius to 48 degrees Celsius. In some embodiments, the fluid can be heated to a temperature in a range of 35 degrees Celsius to 65 degrees Celsius. In some embodiments, the fluid can be heated to a temperature in a range from 38 degrees Celsius to 42 degrees Celsius.

FIG. 2B is an isometric front, side and top view of the second embodiment of the thermal mapping catheter 101' depicted in FIG. 2A. In an example, FIGS. 2C and 2D depict the cross-section of fluid sac 125-C, 125-D and the flexible circuit 128. Fluid sacs 126, 127 can include features similar to those discussed in relation to fluid sac 125. The cross-section (e.g., width and/or height) of fluid sacs 126, 127 can be the same, smaller, or larger than the cross-section of fluid sac 125. FIG. 2C depicts the cross-section of the fluid sac 125-C when the fluid sac 125-C is partially filled with the fluid. For example, the fluid sac 125-C is depicted as partially expanded in FIG. 2C. FIG. 2D depicts the cross-section of the fluid sac 125-D when the fluid sac 125-D is filled to an extent that is greater than that depicted in FIG. 2C. As the fluid sac 125 is filled, the fluid sac 125 can expand, such that a cross-section of the fluid sac 125 forms an oblong shape. In an example, the fluid sac 125 can be filled such that a height of the fluid sac 125 is less than that of the electrodes 106'. Alternatively, the fluid sac 125 can be filled such that a height of the fluid sac 125 is equal to the height of the electrodes 106' and/or is greater than the height of the electrodes 106'.

FIG. 3A is a top view of a third embodiment of the thermal mapping catheter 101". The thermal mapping catheter 101" can include longitudinally extending arms 102", 103", 104", 105", which can form the flexible framework on which ring electrodes 106" are carried. The thermal mapping catheter 101" can also include the catheter shaft 107" and the connector 108". The thermal mapping catheter 101" can include fluid sacs 146, 147, 148, as discussed in relation to FIG. 1A. In some embodiments, the thermal mapping catheter 101" can include a thin film heating element 143, 144, 145. In an example, the thin film heating element can include a thin film layer, which in some embodiments can be a layer formed from silicon. In some embodiments, a conductive layer can be disposed on the thin film, which can form the heating element. For example, the conductive layer can be deposited on the thin film via a deposition process, such as thermal deposition and/or chemical deposition. In some embodiments, the conductive layer can be metal and can be formed in a particular pattern on the thin film. In some embodiments, a temperature sensor 140, 141, 142 can be placed on the film and configured to sense a temperature of the fluid.

Figure 9A:
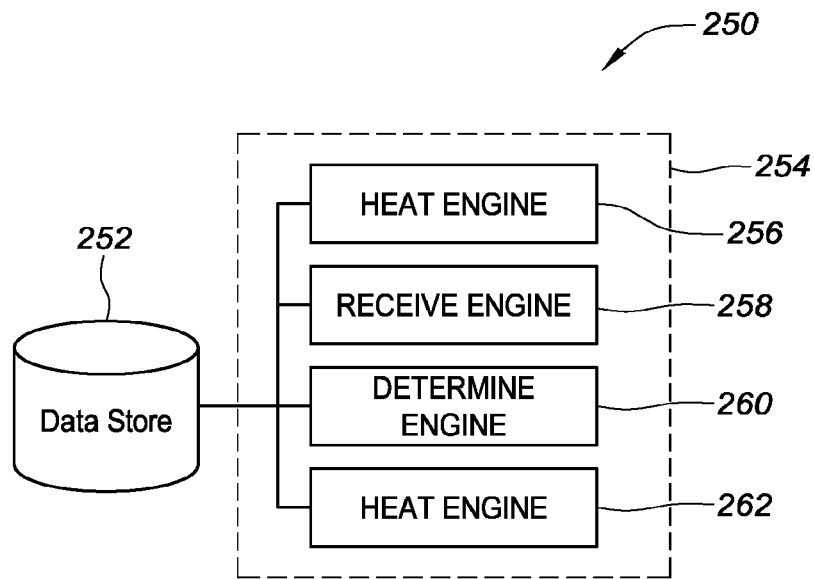
FIG. 9A depicts a diagram of a system for thermal mapping and ablation, according to embodiments of the present disclosure.

In some embodiments, as depicted in FIG. 3A with reference to thin film heating element 143, an electrical lead 149 can connect the thin film heating element 143 to an electrical source or one or more computers comprising a processor and memory storing non-transitory computer-readable instructions executable by the processor and a thermocouple electrical lead 150 can connect the thermocouple 140 to an electrical source and/or the one or more computers, for example such as those discussed in relation to FIGS. 9A and/or 9B.

In some embodiments, as depicted in FIGS. 3A, 3C, and 3D, the thin film heating elements 143, 144, 145 can be planar. The thin film heating elements 143, 144, 145 can be configured to conform to a shape of each one of the fluid sacs 146, 147, 148. With particular reference to thin film heating element 143 and fluid sac 146, the thin film heating element can include flared portions (e.g., flared portion 151), in some embodiments, which conform to points where the fluid sac 146 is attached to the arms (e.g., first inboard arm 103"). Accordingly, by conforming a shape of the thin film heating elements 143, 144, 145 to a shape of a respective one of the fluid sacs 146, 147, 148, fluid contained in each of the fluid sacs 146, 147, 148 can be more uniformly heated. In some embodiments, the thin film heating elements 143, 144, 145 can be connected with a respective one of the fluid sacs 146, 147, 148. For example, the thin film heating elements 143, 144, 145 can be adhered to a wall of a respective one of the fluid sacs 146, 147, 148, with an adhesive. Thus, as the thermal mapping catheter transitions from an undeployed state to a deployed state, the fluid sacs 146, 147, 148 can expand, along with the thin film heating elements 143, 144, 145.

As previously discussed, in some embodiments, the fluid can be heated to a temperature in a range of 50 degrees Celsius to 60 degrees Celsius. However, the fluid can be heated to a temperature less than 50 degrees Celsius and/or greater than a temperature of 60 degrees Celsius. In some embodiments, the fluid can be heated to a temperature of 40 degrees Celsius to 60 degrees Celsius. In some embodiments, the fluid can be heated to a temperature of 40 degrees Celsius to 48 degrees Celsius. In some embodiments, the fluid can be heated to a temperature in a range of 35 degrees Celsius to 65 degrees Celsius. In some embodiments, the fluid can be heated to a temperature in a range from 38 degrees Celsius to 42 degrees Celsius.

In some embodiments, the tissue can be warmed via the fluid sacs 146, 147, 148 to a temperature in a range from 38 degrees Celsius to 42 degrees Celsius, which can cause the tissue to exhibit an ECG pattern recognizable as the Brugada pattern. However, in some embodiments, the tissue can be warmed to a temperature greater than 42 degrees Celsius. For example, in some embodiments, the tissue can be heated to a temperature in a range from 38 degrees Celsius to 45 degrees Celsius, 38 degrees Celsius to 50 degrees Celsius, 42 degrees Celsius to 48 degrees Celsius, and/or 42 degrees Celsius to 50 degrees Celsius.

FIG. 3B is an isometric front, side and top view of the third embodiment of the thermal mapping catheter 101" depicted in FIG. 3A. In some embodiments, the fluid sacs 146, 147, 148 can be attached to the longitudinally extending arms 102", 103", 104", 105". In an example, as the flexible framework is expanded, the fluid sacs 146, 147, 148 can also be expanded and filled with the fluid.

In an example, FIGS. 3C and 3D depict the cross-section of fluid sac 146 and the flexible circuit 143. The cross-section of fluid sacs 147, 148 can be the same, smaller, or larger than the cross-section of fluid sac 146. FIG. 2C depicts the cross-section of the fluid sac 146 when the fluid sac 146 is partially filled with the fluid. For example, the fluid sac 146 is depicted as partially expanded in FIG. 3C. FIG. 3D depicts the cross-section of the fluid sac 146 when the fluid sac 146 is filled to an extent that is greater than that depicted in FIG. 3C. As the fluid sac 146 is filled, the fluid sac 146 can expand, such that a cross-section of the fluid sac 146 forms an oblong shape. In an example, the fluid sac 146 can be filled such that a height of the fluid sac 146 is less than that of the electrodes 106".

FIG. 4 is a top view of a fourth embodiment of a thermal mapping catheter. The thermal mapping catheter 101''' can include longitudinally extending arms 102''', 103''', 104''', 105''', which can form the flexible framework on which ring electrodes 106''' are carried. The thermal mapping catheter 101''' can also include the catheter shaft 107''' and the connector 108'''. In some embodiments, the catheter shaft 107''' can include one or more ring electrodes 167. The thermal mapping catheter 101''' can include fluid sacs 158, 159, 160, as discussed in relation to FIG. 1A.

In some embodiments, each fluid sac 158, 159, 160 can include a heating and temperature sensing assembly. In an example, each heating and temperature sensing assembly can include a proximal electrode 156 and a distal electrode 155, which use a bipolar radio frequency (RF) technique to heat the fluid included in each fluid sac 158, 159, 160. In an example, a temperature sensor 157 can be mounted between the proximal electrode 156 and the distal electrode 155. The fluid in the fluid sacs 158, 159, 160 can be heated to a temperature in a range such as that previously discussed herein. In some embodiments, the tissue can be heated to a temperature in a range such as that previously discussed herein via the fluid sacs 158, 159, 160.

In some embodiments, the proximal electrode 156, the distal electrode 155, and the temperature sensor 157 can be mounted on a support structure 161. Other support structures (e.g., support structures 162, 163) can support additional temperature sensors and thermocouples disposed in the fluid sacs 159, 158. In an example, with particular reference to the support structure 161, the structure can be formed from a non-conductive material, such that each electrode 155, 156 is insulated from one another. In some examples, the support structure 161 can be a wire made of nitinol. In some embodiments, the support structure 161 can be a tube through which wires run to provide electrical connections to the proximal electrode 156, distal electrode 155, and the temperature sensor 157. Alternatively, the wires can run along the outside of the support structure 161. In some embodiments, an irrigation pathway can run through the support structure 161 and can be configured to provide fluid to the fluid sacs 158, 159, 160.

In some embodiments, the temperature sensor 157 can be disposed off-axis with respect to the support structure 161. In an example, an off-axis thermocouple lead and/or tube 164 that houses a lead can extend from the support structure 161 and can electromechanically couple the temperature sensor 157.

In some embodiments, a width of the inside of each fluid sac, defined by line A can be approximately 2.25 millimeters (mm), although the width can be smaller or larger than 2.25 mm. In some embodiments, a length of each fluid sac, defined by line B, can be approximately 15.5 mm, although the length can be smaller or larger than 15.5 mm. In some embodiments, a length of each fluid sac between the distal end of each fluid sac to the distal end of the connector 108''', defined by line C can be approximately 20.5 mm, although the length can be smaller or larger than 20.5 mm.

In some embodiments, as depicted in FIG. 4, the thermal mapping catheter 101''' can include a fluid sac support structure 165. In an example, the fluid sac support structure 165 can be a unitary piece of material, a first end of which extends distally from a distal end of the connector 108''' and extends along an inner surface of the first outboard arm 102'''. A distal end of the fluid sac support structure 165 can extend towards the first inboard arm 103''' and proximally along an outer surface of the first inboard arm 103''' before crossing over a proximal portion of the first inboard arm 103''' and extending distally along an inner surface of the first inboard arm 103'''. The support structure 165 can repeat this pattern along the inner and/or outer surfaces of the second inboard arm 104''' and second outboard arm 105'''. In some embodiments, the support structure can be located within the fluid sacs 158, 159, 160 and can aid in expansion of the fluid sacs 158, 159, 160 upon deployment of the thermal mapping catheter 101'''. In some embodiments, the fluid sacs 158, 159, 160 can include one or more fluid sac mounting portions (e.g., fluid sac mounting portions 166-1, 166-2). The fluid sac mounting portions 166-1, 166-2 can connect the fluid sacs 158, 159, 160 to one or more of the first outboard arm 102''', first inboard arm 103''', second inboard arm 104''', and second outboard arm 105'''. In an example, each fluid sac 158, 159, 160 can include one or more fluid sac mounting portions 166-1, 166-2 that can be configured to connect the fluid sacs 158, 159, 160 to the arms. In some embodiments, each fluid sac mounting portion 166-1, 166-2 can be a band of material that encircles a portion of a respective arm. For example, fluid sac mounting portion 166-1 can encircle the second outboard arm 105''' along a portion of the arm located between electrodes 106-1, 106-2. In some embodiments, the fluid sac mounting portion can be formed from a same material that forms the fluid sacs and the fluid sacs and mounting portion can be unitary in construction.

In some embodiments, fluid sac mounting portion 166-2 can connect adjacent fluid sacs (e.g., fluid sacs 158, 159) to an arm (e.g., first inboard arm 103''). In an example, the fluid sac mounting portion 166-2 can be connected to both of the fluid sacs 158, 159 and can encircle the first inboard arm located between the fluid sacs 158, 159. The fluid sac mounting portion 166-2 can encircle a portion of the first inboard arm 103''' located between electrodes disposed on the first inboard arm 103''', as previously discussed. In some embodiments, the fluid sacs 158, 159, 160 can be connected to one another at a proximal portion of the fluid sacs, as depicted in FIG. 4. Because the fluid sacs 158, 159, 160 are proximally connected, the fluid sacs 158, 159, 160 can be in fluid communication with each other. In some embodiments, a distal end of the connector 108''' can include a fluid lumen that is in fluid communication with the fluid sacs 158, 159, 160 and can be configured to transfer fluid into or out of the fluid sacs 158, 159, 160.

FIG. 5A is a top view of a fifth embodiment of a thermal mapping catheter 170 with a first number of electrodes. The thermal mapping catheter 170 can include longitudinally extending arms 172, 173, 174, 175, 176, 177, which can form the flexible framework on which ring electrodes 171 are carried. In some embodiments, the flexible framework can include 64 electrodes 171. Although 64 electrodes are depicted, greater than or fewer than 64 electrodes can be disposed on the flexible framework. The thermal mapping catheter 170 can also include the catheter shaft 180 and the connector 178. In some embodiments, the catheter shaft 180 can include one or more ring electrodes 179.

In some embodiments, the catheter shaft 180 can include an irrigation channel, which is in fluid communication with an irrigation port 181. In an example, fluid 182 (e.g., saline solution), can travel through the irrigation channel and can be expelled through the irrigation port 181. In an example, the fluid 182 can be heated before the fluid 182 is expelled through the irrigation port 181 or can be heated as the fluid 182 passes through the port 181. The fluid 182 can be heated to a temperature in a range such as that previously discussed in relation to FIGS. 1-4. For example, the fluid 182 can be heated to a temperature in a range from 50 degrees Celsius to 60 degrees Celsius. However, the fluid can be heated to a temperature less than 50 degrees Celsius and/or greater than a temperature of 60 degrees Celsius. In some embodiments, the fluid can be heated to a temperature in a range from 40 degrees Celsius to 60 degrees Celsius. In some embodiments, the fluid can be heated to a temperature in a range from 40 degrees Celsius to 48 degrees Celsius. In some embodiments, the fluid can be heated to a temperature in a range from 35 degrees Celsius to 65 degrees Celsius. In some embodiments, the fluid can be heated to a temperature in a range from 38 degrees Celsius to 42 degrees Celsius.

In contrast, instead of the fluid being introduced into a fluid sac, the fluid can be expelled from the irrigation port 181 and can directly contact tissue. The fluid 182 can be expelled from the irrigation port 181 such that the fluid 182 substantially covers the electrodes 171. For example, the fluid 182 can be expelled such that it reaches the distal most electrodes 171. In some embodiments, the irrigation port 181 can have a greater width than a height, forming a planar irrigation port configured to expel a flow (e.g., fan shaped flow) of fluid 182 over the electrodes 171 disposed on the flexible framework, as depicted.

FIG. 5B is a top view of a fifth embodiment of the thermal mapping catheter 170' with a second number of electrodes. The thermal mapping catheter 170' can include longitudinally extending arms 172', 173', 174', 175', 176', 177', which can form the flexible framework on which ring electrodes 171' are carried. In some embodiments, the flexible framework can include 32 electrodes 171'. Although 32 electrodes are depicted, greater than or fewer than 32 electrodes can be disposed on the flexible framework. The thermal mapping catheter 170' can also include the catheter shaft 180' and the connector 178'. In some embodiments, the catheter shaft 180' can include ring electrodes 179'.

The thermal mapping catheter can include an irrigation port 181', as discussed in relation to FIG. 5A, which can be configured to expel fluid 182' over the electrodes 171' disposed on the flexible framework, as depicted. The fluid 181' can warm tissue that is located adjacent to the electrodes 171', which can help unmask the Brugada pattern, as discussed herein. For example, the tissue can be warmed via the fluid 181' to a temperature in a range from 38 degrees Celsius to 42 degrees Celsius, which can cause the tissue to exhibit an ECG pattern recognizable as the Brugada pattern. However, in some embodiments, the tissue can be warmed to a temperature greater than 42 degrees Celsius. For example, in some embodiments, the tissue can be heated to a temperature in a range from 38 degrees Celsius to 45 degrees Celsius, 38 degrees Celsius to 50 degrees Celsius, 42 degrees Celsius to 48 degrees Celsius, and/or 42 degrees Celsius to 50 degrees Celsius.

Figure 5D:
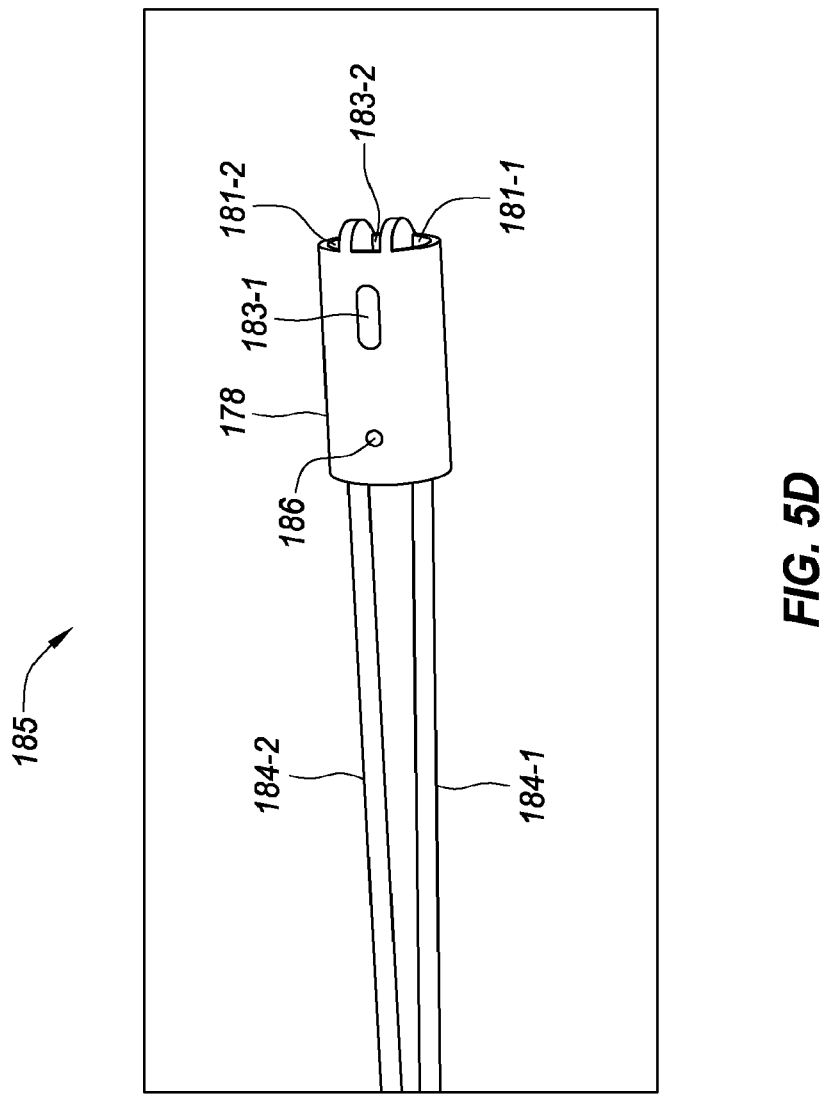
FIG. 5D is a side view of an irrigation assembly shown in FIGS. 5A to 5C, according to various embodiments of the present disclosure.

FIG. 5C is an isometric front, side and top view of the fifth embodiment of the thermal mapping catheter 170 shown in FIG. 5A, according to various embodiments of the present disclosure. FIG. 5C further depicts the irrigation port 181, discussed in relation to FIGS. 5A and 5B, which is configured to direct fluid over the flexible framework. FIG. 5D is a side view of an irrigation assembly 185 shown in FIGS. 5A to 5C, according to various embodiments of the present disclosure. The irrigation assembly 185 can include a first irrigation lumen 184-1 and second irrigation lumen 184-2, which feed fluid 182 to a first irrigation port 181-1 and a second irrigation port 181-2. The irrigation ports can expel the fluid 182 over each side of the flexible support structure (e.g., flexible framework, planar array), shown in FIG. 5A. In some embodiments, the irrigation lumens 184-1, 184-2 can be made from a flexible, rigid, and/or semi-rigid material. For example, in some embodiments the irrigation lumens 184-1, 184-2 can be formed from plastic or metal. In some embodiments, and as depicted, the irrigation ports 181-1, 181-2 can be planar in shape (i.e., can have a greater width than a height), thus creating a generally planar fluid flow over the flexible framework. In some embodiments, a plane defined by each of the irrigation ports 181-1, 181-2 (e.g., distal opening of the irrigation ports 181-1, 181-2) can be parallel with a plane defined by the flexible support structure (e.g., planar array). This can enable the fluid 182 to be broadcast evenly over the planar array and the electrodes disposed thereon.

The irrigation assembly 185 can include the connector 178, which can includes sockets 183-1, 183-2 in which the longitudinally extending arms can be inserted and secured.

A third socket can be disposed on a diametrically opposed side to a first socket 183-1, and is hidden from view. In some embodiments, the connector 178 can include a connection socket 186, through which a pin can be inserted to secure the connector to the distal end of the catheter shaft 180.

In some embodiments, the fluid 182' can be expelled from the irrigation port 181' such that the fluid 182' substantially covers the electrodes 171. The heated fluid can cause the cardiac tissue to display the signs that are indicative of BrS. In some embodiments, the electrodes 171 can be used for mapping and/or ablation. For example, the electrodes can be used to monitor mapping signals produced by the tissue. In some embodiments, the mapping signals can exhibit an electrical pattern that can be associated with Brugada syndrome. In some embodiments, the electrodes can monitor mapping signals produced by the tissue while the fluid 182' is being expelled from the irrigation port 181', during a portion of the time while the fluid 182' is being expelled from the irrigation port 181', and/or before or after the fluid 182' has been expelled from the irrigation port 181'.

Figure 6A:
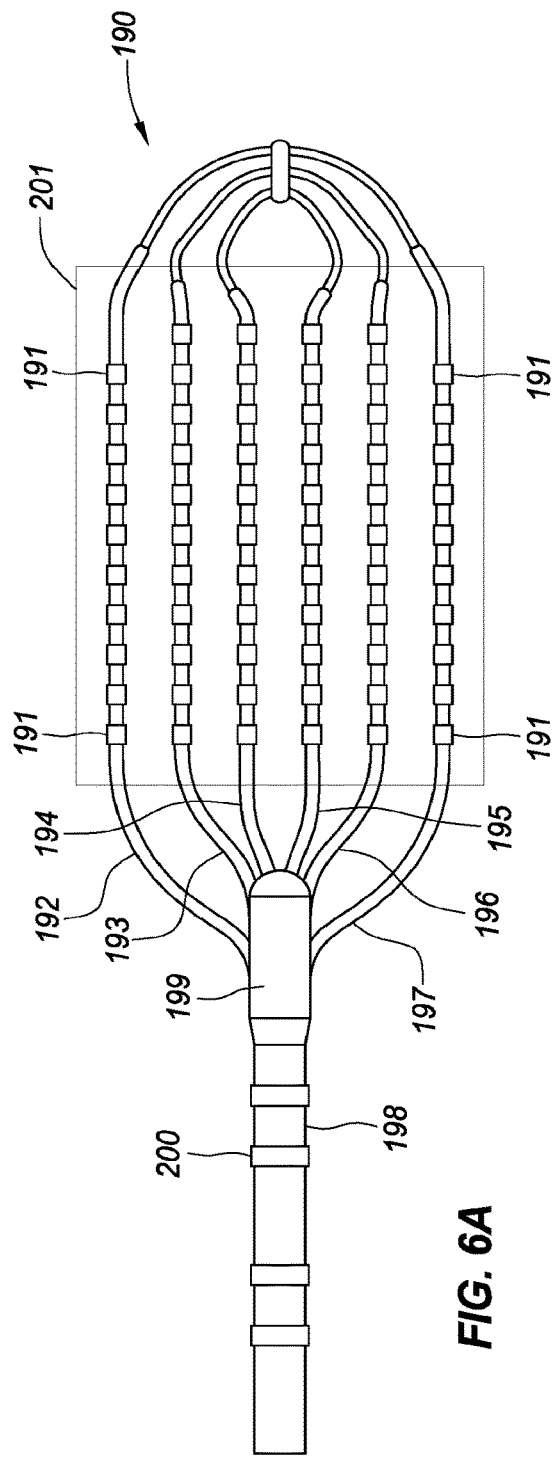
FIG. 6A is a top view of a sixth embodiment of a thermal mapping catheter with a first number of electrodes, according to various embodiments of the present disclosure.

FIG. 6A is a top view of a sixth embodiment of a thermal mapping catheter 190 with a first number of electrodes. The thermal mapping catheter 190 can include longitudinally extending arms 192, 193, 194, 195, 196, 197, which can form the flexible framework on which ring electrodes 191 are carried. In some embodiments, the flexible framework can include 64 electrodes 191, although fewer than or greater than 64 electrodes can be disposed on the flexible framework. The thermal mapping catheter 190 can also include the catheter shaft 198 and the connector 199. In some embodiments, the catheter shaft 198 can include one or more ring electrodes 200.

In some embodiments, the electrodes 191 can deliver RF energy 201 at a decreased level as that associated with performing ablation to heat the cardiac tissue. In some embodiments, one or more temperature sensors can be disposed on the flexible framework and can enable the electrodes 191 to heat the cardiac tissue to a temperature range as discussed herein for the diagnosis of BrS. In an example, the temperature sensors can be disposed in one or more of the electrodes 191. In some embodiments, the electrodes 191 can be in communication (e.g., electrically coupled) with an energy source (e.g., radiofrequency (RF) generator), which can be configured to deliver energy (e.g., RF energy) to tissue (e.g., cardiac tissue) via one or more of the electrodes 191, which can cause the tissue to be heated. Some embodiments of the present disclosure can be configured to deliver unipolar RF energy to tissue via the electrodes 191. For example, unipolar RF energy can be delivered to one or more of the electrodes 191 and the RF energy can travel through the tissue to a patch, usually located on a back of the patient, in order to heat the tissue and/or electrodes 191.

Figure 6B:
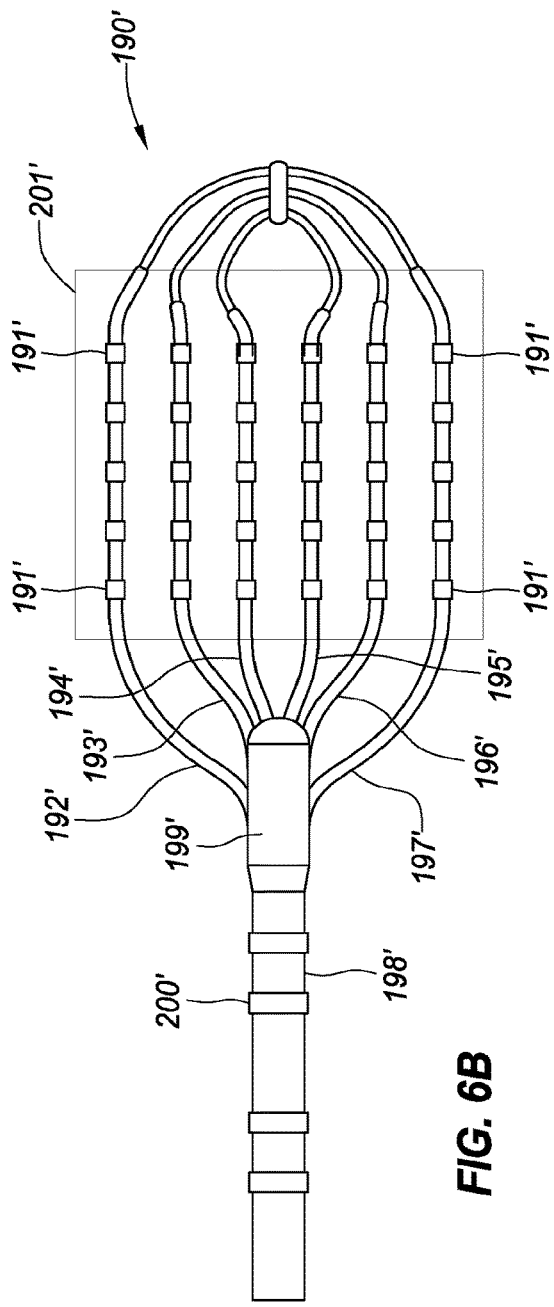
FIG. 6B is a top view of a sixth embodiment of the thermal mapping catheter with a second number of electrodes, according to various embodiments of the present disclosure.

FIG. 6B is a top view of a sixth embodiment of the thermal mapping catheter 190' with a second number of electrodes. The thermal mapping catheter 190' can include longitudinally extending arms 192', 193', 194', 195', 196', 197', which can form the flexible framework on which ring electrodes 191' are carried. In some embodiments, the flexible framework can include 32 electrodes 191'. The thermal mapping catheter 190' can also include the catheter shaft 198' and the connector 199'. In some embodiments, the catheter shaft 198' can include ring electrodes 200'. As discussed in relation to FIG. 6A, the electrodes 191 can deliver RF energy at a decreased level as that associated with performing ablation to heat the cardiac tissue and can be controlled based on feedback received from one or more temperature sensors disposed on the flexible framework.

In some embodiments, the electrodes (e.g., electrodes 201, 201') associated with the embodiments depicted in FIGS. 6A and 6B can be heated to a particular temperature and/or for a particular time. The electrodes can be disposed against a tissue (e.g., cardiac tissue) to cause the tissue to be heated in order to unmask the Brugada pattern. In some embodiments, the electrodes can be heated to a temperature in a range from 50 degrees Celsius to 60 degrees Celsius. However, the electrodes can be heated to a temperature less than 50 degrees Celsius and/or greater than 60 degrees Celsius. For example, the electrodes can be heated to a temperature in a range of 35 degrees Celsius to 65 degrees Celsius. In some embodiments, the electrodes can be heated to a temperature in a range from 38 degrees Celsius to 42 degrees Celsius.

In some embodiments, the electrodes can be heated to warm an adjacent tissue and then turned off to perform a mapping function. In some embodiments, the tissue can be warmed via the electrodes to a temperature in a range from 38 degrees Celsius to 42 degrees Celsius, which can cause the tissue to exhibit an ECG pattern recognizable as the Brugada pattern. However, in some embodiments, the tissue can be warmed to a temperature greater than 42 degrees Celsius. For example, in some embodiments, the tissue can be heated to a temperature in a range from 38 degrees Celsius to 45 degrees Celsius, 38 degrees Celsius to 50 degrees Celsius, 42 degrees Celsius to 48 degrees Celsius, and/or 42 degrees Celsius to 50 degrees Celsius.

Figure 7:
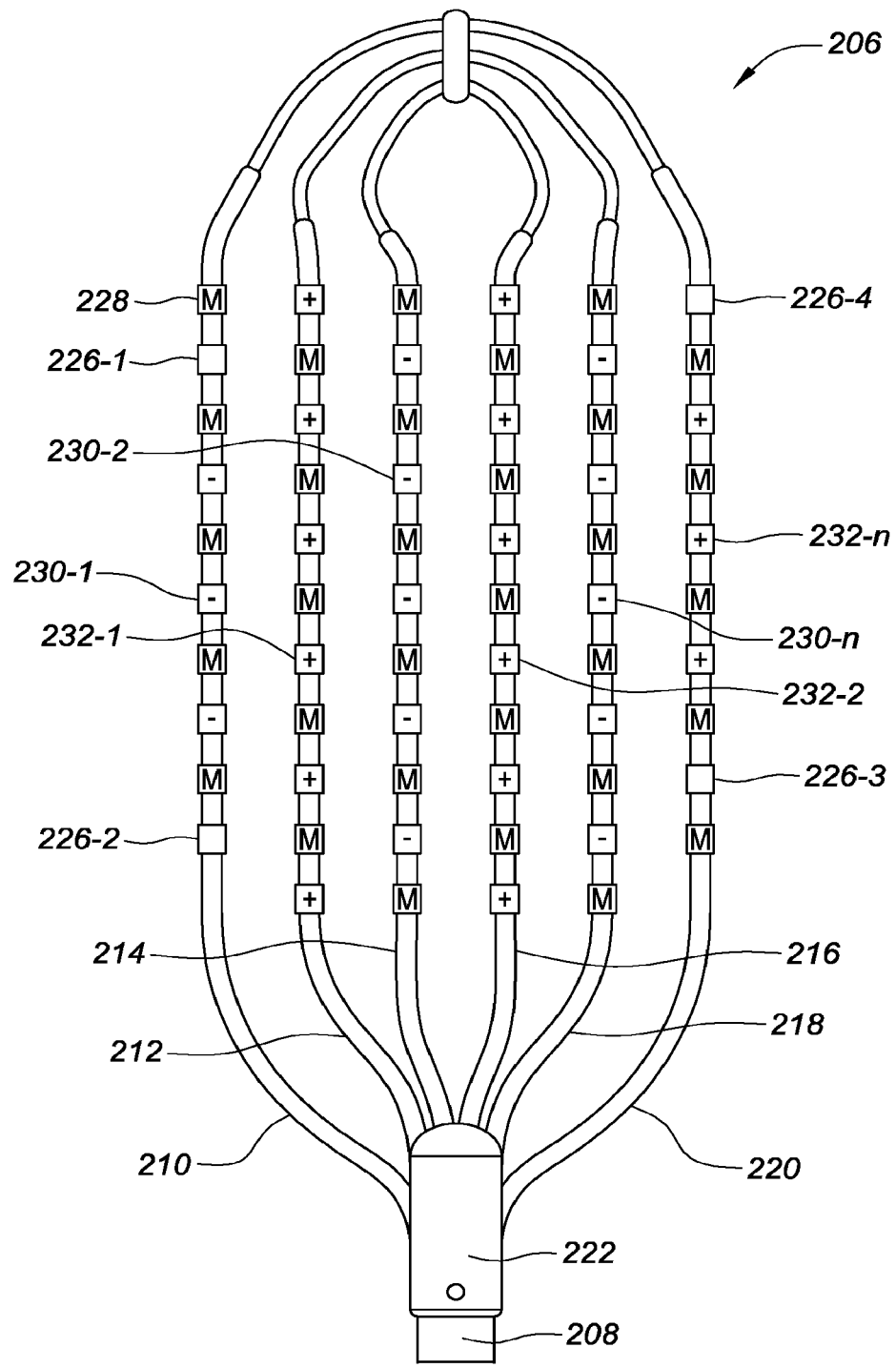
FIG. 7 is a top view of a thermal mapping catheter that includes mapping electrodes, heating electrodes, and thermocouples, according to various embodiments of the present disclosure.

FIG. 7 depicts a combination thermal mapping and ablation catheter 206, according to various embodiments of the present disclosure. In some embodiments, the thermal mapping and ablation catheter 206 can include longitudinally extending arms 210, 212, 214, 216, 218, 220, which can form a flexible framework (e.g., planar array) on which a number of electrodes can be disposed. In some embodiments, the thermal mapping and ablation catheter can include greater than or less than six longitudinally extending arms. In an example, the number of electrodes can include a number of heating electrodes, that include negative heating electrodes 230-1, 230-2, 230-$n$ (hereinafter generally referred to as negative heating electrodes 230), designated by a negative symbol in FIG. 7, and a number of positive heating electrodes 232-1, 232-2, 232-$n$ (hereinafter generally referred to as positive heating electrodes 232), designated by a positive symbol in FIG. 7. In some embodiments, the negative heating electrodes 230 and positive heating electrodes 232 can be disposed on alternating longitudinally extending arms. For example, as depicted, negative heating electrodes 230 can be disposed on a first outboard arm 210; positive heating electrodes 232 can be disposed on a first medial arm 212; negative heating electrodes 230 can be disposed on a first inboard arm 214; positive heating electrodes 232 can be disposed on a second inboard arm 216; negative heating electrodes 230 can be disposed on a second medial arm 218; and positive heating electrodes 232 can be disposed on a second outboard arm 220.

In some embodiments, the negative heating electrodes 230 and the positive heating electrodes 232 can be in communication with an energy source (e.g., radiofrequency (RF) generator), which can be configured to deliver energy (e.g., RF energy) to tissue (e.g., cardiac tissue) via one or more of the electrodes 230, 232, which can cause the tissue to be heated. Some embodiments of the present disclosure can be configured to deliver multipolar (e.g., bipolar) RF energy to tissue via the electrodes 230, 232. For example, bipolar RF energy can be delivered to one or more of the positive heating electrodes 232 and the RF energy can travel through the tissue to one or more of the negative heating electrodes 230 in order to heat the tissue and/or electrodes 230, 232.

In some embodiments, mapping electrodes 228, designated as 'M' in FIG. 7, can be disposed on one or more of the longitudinally extending arms 210, 212, 214, 216, 218, 220. In an example, and as depicted, the mapping electrodes 228 can be disposed on each of the longitudinally extending arms 210, 212, 214, 216, 218, 220. In some embodiments, the heating electrodes and the mapping electrodes 228 can be disposed on each of the longitudinally extending arms 210, 212, 214, 216, 218, 220 in a longitudinally alternating pattern. For example, each of the heating electrodes can be separated from an adjacent heating electrode disposed on one of the arms via a mapping electrode, as depicted in FIG. 7. For example, with reference to the first outboard arm 210, the negative heating electrodes 230 can be separated by the mapping electrodes 228. With reference to the first medial arm 212, the positive heating electrodes 232-1 can be separated by the mapping electrodes 228. In some embodiments, the positive heating electrodes 232 and the negative heating electrodes 230 can be disposed on each of the longitudinally extending arms 210, 212, 214, 216, 218, 220 in a transversely alternating pattern. For example, each of the heating electrodes can be separated from an adjacent heating electrode disposed on an adjacent arm via a mapping electrode 228, as depicted in FIG. 7. In some embodiments, half of the electrodes can be mapping electrodes 228 and half of the electrodes can be heating electrodes.

In some embodiments, one or more thermocouples can be disposed along one or more of the longitudinally extending arms 210, 212, 214, 216, 218, 220. As depicted, thermocouples 226-1, 226-2, 226-3, 226-4 can be located in proximal and distal quadrants of the flexible framework of the thermal mapping and ablation catheter 206. For example, the thermocouples 226-1, 226-2, 226-3, 226-4 can be disposed on a proximal and distal portion of each of the first outboard arm 210 and the second outboard arm 220. However, thermocouples can be disposed along other portions of the first outboard arm 210 and the second outboard arm 220, as well as along other portions of the longitudinally extending arms forming the flexible framework. In some embodiments, the thermocouples can be disposed on or adjacent to heating electrodes. For example, thermocouples 226-1, 226-2 can be disposed on negative heating electrodes and thermocouples 226-3, 226-4 can be disposed on positive heating electrodes.

In some embodiments, the heating electrodes (e.g., negative electrodes 230 and positive electrodes 232) can be warmed to a temperature that is configured to unmask the Brugada pattern (e.g., a pattern recognizable in an ECG). In an example, the electrodes can be heated to a temperature in a range previously disclosed herein. The temperature can be defined by a user, in some embodiments, and/or may be pre-programmed into computer executable instructions. In some embodiments, the heating electrodes can be heated to a temperature in a range of 50 degrees Celsius to 60 degrees Celsius. However, the heating electrodes can be heated to a temperature less than 50 degrees Celsius and/or greater than 60 degrees Celsius. For example, the heating electrodes can be heated to a temperature in a range of 35 degrees Celsius to 65 degrees Celsius. In some embodiments, the heating electrodes can be heated to a temperature in a range from 38 degrees Celsius to 42 degrees Celsius. In some embodiments, the tissue can be warmed via the electrodes to a temperature in a range from 38 degrees Celsius to 42 degrees Celsius, which can cause the tissue to exhibit an ECG pattern recognizable as the Brugada pattern. However, in some embodiments, the tissue can be warmed to a temperature greater than 42 degrees Celsius. For example, in some embodiments, the tissue can be heated to a temperature in a range from 38 degrees Celsius to 45 degrees Celsius, 38 degrees Celsius to 50 degrees Celsius, 42 degrees Celsius to 48 degrees Celsius, and/or 42 degrees Celsius to 50 degrees Celsius.

In some embodiments, the thermocouples 226-1, 226-2, 226-3, 226-4 can provide feedback regarding a temperature to which the electrodes have been heated and/or to which tissue being heated by the electrodes has been heated. The feedback can be analyzed to control an amount of RF energy provided to the electrodes in order to vary their temperature based on the feedback. At a same time that the heating electrodes are heated, before the heating electrodes are heated, and/or after the heating electrodes are heated, the mapping electrodes 228 can collect ECG data from the tissue. In some embodiments, the mapping electrodes 228 can collect ECG data from the tissue that has been warmed (e.g., tissue located in a pericardial region of the heart). The ECG data can be analyzed to determine whether the ECG data exhibits the Brugada pattern.

In some embodiments, the heating electrodes can be heated to a particular temperature for a particular period of time. In an example, the heating electrodes can be heated to an upper limit temperature for a particular period of time and then to a lower limit temperature for a particular period of time. Accordingly, the heating electrodes can heat tissue to a temperature between the upper limit temperature and the lower limit temperature. In some embodiments, the upper limit temperature can be a temperature associated with the performance of ablation. However, the heating electrodes can be heated to the upper limit temperature for a period of time that does not result in the tissue being heated to the temperature associated with the performance of ablation. In some embodiments, as the upper limit temperature is increased, the time period for which the heating electrode is heated to the upper limit temperature can be decreased and/or a time period for which the heating electrode is heated to the lower limit temperature can be increased. As such, even though the heating electrodes may be heated to a temperature associated with the performance of ablation, the tissue being heated by the heating electrodes may be heated to a lower temperature at which the tissue may exhibit a pattern that is associated with BrS (e.g., a temperature between the upper limit temperature and the lower limit temperature).

In some embodiments, one or more of the heating electrodes can receive an increased RF energy, which can cause the heating electrodes to be heated to a temperature sufficient to perform a therapeutic treatment (e.g., ablation). In some embodiments, the temperature sufficient to perform therapeutic treatment can be in a range from 42 degrees Celsius to 70 degrees Celsius, however the temperature can be greater than 70 degrees Celsius or less than 42 degrees Celsius. In some embodiments, the heating electrodes can be heated to a temperature in a range from 50 degrees Celsius to 70 degrees Celsius, 60 degrees Celsius to 70 degrees Celsius, and/or 65 degrees Celsius to 70 degrees Celsius to perform therapeutic treatment (e.g., a temperature between the upper limit temperature and the lower limit temperature). In some embodiments, the one or more of the heating electrodes can be selected to receive an increased RF energy in response to a Brugada pattern being recognized in the ECG data. Thus, the thermal mapping and ablation catheter

206 can be configured to controllably heat tissue (e.g., cardiac tissue) with the heating electrodes to cause the tissue to exhibit an ECG pattern recognizable as the Brugada pattern. The thermal mapping and ablation catheter 206 can be configured to detect the ECG pattern with the mapping electrodes 228, in order to identify the Brugada pattern. Additionally, in some embodiments, the thermal mapping and ablation catheter 206 can heat a selected number of the heating electrodes to a temperature consistent with the performance of tissue ablation.

Figure 8:
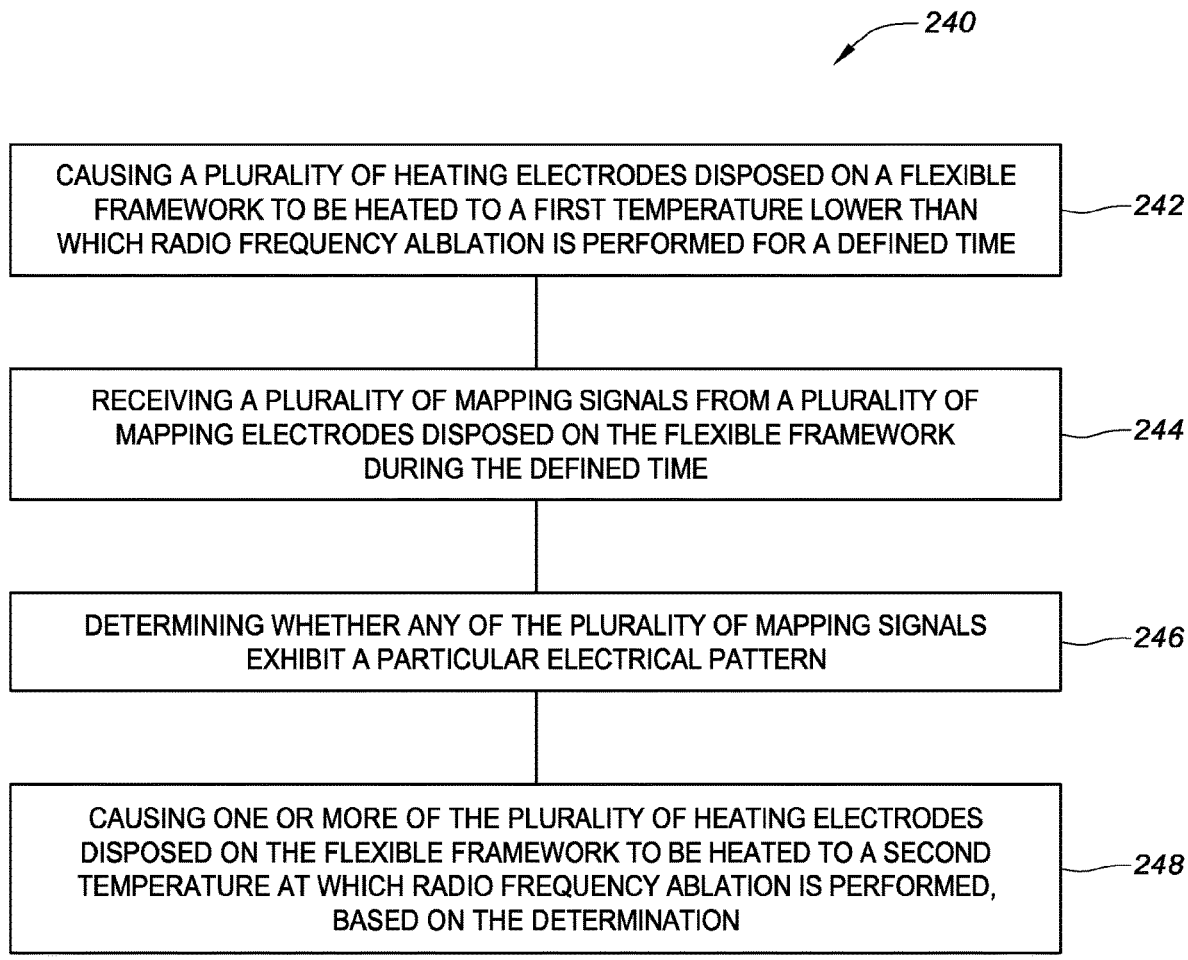
FIG. 8 depicts a flow diagram associated with a method, according to various embodiments of the present disclosure.

FIG. 8 depicts a flow diagram associated with a method 240 for thermal mapping and ablation, according to various embodiments of the present disclosure. The method 240 can be performed in relation to embodiments discussed herein, such as those discussed in FIGS. 6A to 7. In some embodiments, the method 240 can include causing a plurality of heating electrodes disposed on a flexible framework to be heated to a first temperature lower than which radio frequency ablation is performed for a defined time, at block 242. The defined time can be selectable by a user, in some embodiments. In an example, the electrodes can contact tissue (e.g., epicardial tissue) and the tissue can be heated to a temperature in a range, such as that previously discussed, to cause the tissue to be heated in order to unmask the Brugada pattern.

In some embodiments, at block 244, the method 240 can include receiving a plurality of mapping signals from a plurality of mapping electrodes disposed on the flexible framework during the defined time. In some embodiments, the mapping signals from the plurality of mapping electrodes disposed on the flexible framework can be received during a portion of the defined time. The mapping signals can be electrical signals (e.g., ECG signals), which can be analyzed to determine whether any of the plurality of mapping signals exhibit a particular electrical pattern, at block 246. In an example, a filter can be applied to the mapping signals to determine whether one or more of the mapping signals exhibit a pattern that is associated with BrS.

In some embodiments, the method 240 can include causing one or more of the plurality of heating electrodes disposed on the flexible framework to be heated to a second temperature at which radio frequency ablation is performed, based on the determination, at block 248. In an example, the method 240 can include causing one or more of the plurality of heating electrodes to be heated to the temperature at which radio frequency ablation is performed in response to a determination that one or more of the mapping signals exhibit the particular electrical pattern. In some embodiments, upon recognition that one or more of the mapping signals exhibit the particular electrical pattern, an indication can be displayed to a user (e.g., via a user interface) and/or the heating electrodes can be heated to the temperature at which radio frequency ablation is performed automatically.

In some embodiments, the method 240 can include causing one or more of the plurality of heating electrodes disposed adjacent to one or more of the mapping electrodes from which a mapping signal exhibiting the particular pattern is received to be heated to the second temperature. Thus, tissue that exhibits the particular pattern (e.g., pattern associated with BrS) can be precisely targeted. For example, while the thermal mapping and ablation catheter 206, depicted in FIG. 7 includes 32 mapping electrodes 228, only some of the mapping electrodes 228 may contact tissue that exhibits an electrical pattern associated with BrS. Accordingly, heating electrodes surrounding those mapping electrodes 228 that have collected electrical signals exhibiting patterns associated with BrS can be heated to a temperature at which radio frequency ablation is performed. Thus, the tissue producing the electrical signals exhibiting patterns associated with BrS can be ablated via the electrodes surrounding the mapping electrodes 228. As previously discussed and depicted in relation to FIG. 7, one or more of the plurality of heating electrodes can be disposed at least one of longitudinally adjacent and transversely adjacent to one or more of the mapping electrodes, with respect to a longitudinal axis of the catheter and/or flexible framework on which the electrodes are disposed. In some embodiments, the method 240 can include causing one or more of the plurality of heating electrodes disposed on a particular section of the flexible framework to be heated to a second temperature at which radio frequency ablation is performed. In an example, heating electrodes disposed on a proximal half, distal half, left side, right side, center, and/or combination thereof can be heated to the second temperature.

In some embodiments, after radio frequency ablation is performed, the method can be repeated, for example, to check whether the tissue still exhibits the pattern associated with BrS. For instance, the heating electrodes can be heated to the first temperature and the tissue can be mapped via the mapping electrodes to determine whether any of the plurality of mapping signals received from the mapping electrodes exhibit the pattern associated with BrS. Radio frequency ablation can be performed, as discussed herein, in response to one or more of the plurality of mapping signals exhibiting the pattern associated with BrS.

FIG. 9A depicts a diagram of a system 250 for thermal mapping and ablation, according to embodiments of the present disclosure. The system 250 can include a data store 252, a thermal mapping and/or ablation system 254, and/or a number of engines. The thermal mapping and/or ablation system 254 can be in communication with the data store 252. The thermal mapping and/or ablation system 254 can include a number of engines (e.g., heat engine 256, receive engine 258, determine engine 260, heat engine 262, etc.). The thermal mapping and/or ablation system 254 can include additional or fewer engines than illustrated to perform the various functions described herein. The number of engines can include a combination of hardware and programming to perform a number of functions described herein (e.g., receiving, determining, etc.). Each of the engines can include hardware or a combination of hardware and programming designated or designed to execute a module (e.g., a particular module). The programming can include instructions (e.g., software, firmware, etc.) stored in a memory resource (e.g., computer-readable medium) as well as a hard-wired program (e.g., logic).

Figure 9B:
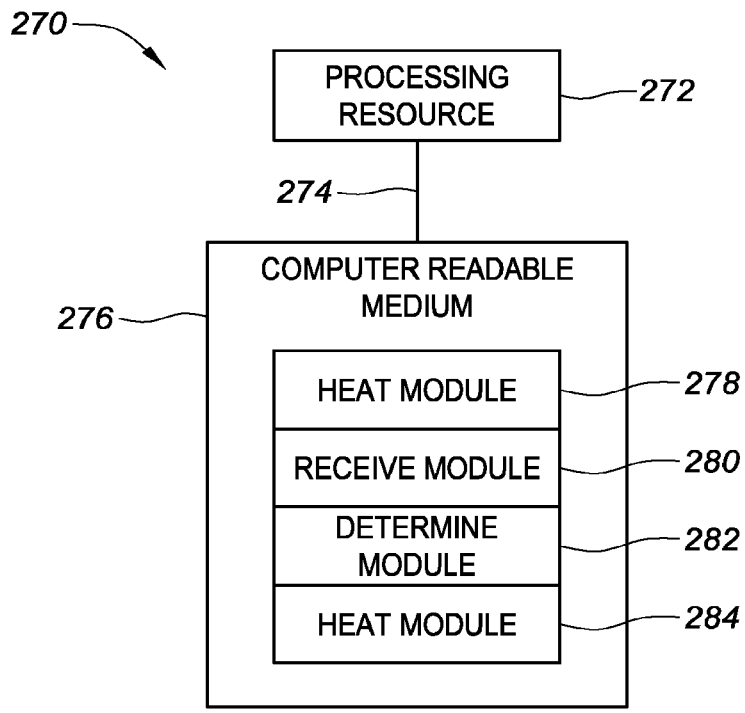
FIG. 9B depicts a diagram of an example of a computing device for thermal mapping and ablation, according to various embodiments of the present disclosure.

The system 254 can include a computing device analogous to that discussed herein and with respect to FIG. 9B. In some embodiments, the computing device can include a digital display such as a graphical user interface (GUI), which is suitable for the display of electronic data. A user interface can include hardware components and/or computer-readable instruction components. For instance, hardware components can include input components (e.g., a mouse, a touchscreen, a keyboard, dials and buttons, etc.) and/or output components (e.g., a display, vibration generating devices, speakers, etc.). An example user interface can include a GUI, which can digitally represent data associated with thermal mapping and/or ablation.

The heat engine 256 can include hardware and/or a combination of hardware and programming to cause a plurality of heating electrodes disposed on a flexible framework to be heated to a first temperature lower than which radio frequency ablation is performed for a defined time. In some embodiments, a particular amount of RF energy can be generated and applied to one or more of the plurality of heating electrodes in order to cause the one or more heating electrodes to be heated. In some embodiments, a temperature sensor (e.g., thermocouple) can sense a particular temperature of one or more of the electrodes and/or tissue being heated by the one or more of the electrodes. In some embodiments, the temperature of the one or more of the temperature sensors can be provided as feedback to the system 254 to adjust a particular amount of RF energy provided to the one or more heating electrodes.

The receive engine 258 can include hardware and/or a combination of hardware and programming to receive a plurality of mapping signals from a plurality of mapping electrodes disposed on the flexible framework during a portion of the defined time. In some embodiments, electrical signals produced by the cardiac tissue (e.g., epicardial tissue) can be mapped while the tissue is being heated to the first temperature (e.g., temperature lower than which radio frequency ablation is performed). In some embodiments, the plurality of mapping signals can be received during an entirety of the defined time or for a time that is less than the entirety of the defined time.

The determine engine 260 can include hardware and/or a combination of hardware and programming to determine whether any of the plurality of mapping signals exhibit a particular electrical pattern. In some embodiments, as discussed herein, a filter can be applied to the mapping signals to determine whether one or more of the plurality of mapping signals exhibit a particular electrical pattern associated with BrS.

The heat engine 262 can include hardware and/or a combination of hardware and programming to causing one or more of the plurality of heating electrodes disposed on the flexible framework to be heated to a second temperature at which radio frequency ablation is performed, based on the determination. In some embodiments, the plurality of heating electrodes can be heated to the second temperature for a second defined time period. In some embodiments, mapping signals can be received from the mapping electrodes while the heating electrodes are being heated to the second temperature and/or after the heating electrodes have been heated to the second temperature, to ensure that tissue responsible for producing the electrical pattern associated with BrS has been ablated.

FIG. 9B depicts a diagram of an example of a computing device 270 for thermal mapping and ablation according to the present disclosure. The computing device 270 can utilize software, hardware, firmware, and/or logic to perform a number of functions described herein.

The computing device 270 can be a combination of hardware and instructions to share information. The hardware, for example can include a processing resource 272 and/or a memory resource 276 (e.g., computer-readable medium (CRM), database, etc.). A processing resource 272, as used herein, can include a number of processors capable of executing instructions stored by the memory resource 276. Processing resource 272 can be integrated in a single device or distributed across multiple devices. The instructions (e.g., computer-readable instructions (CRI)) can include instructions stored on the memory resource 276 and executable by the processing resource 272 to implement a desired function (e.g., determine whether any of the plurality of mapping signals exhibit a particular electrical pattern, etc.).

The memory resource 276 can be in communication with the processing resource 272. The memory resource 276, as used herein, can include a number of memory components capable of storing instructions that can be executed by the processing resource 272. Such memory resource 276 can be a non-transitory CRM. Memory resource 276 can be integrated in a single device or distributed across multiple devices. Further, memory resource 276 can be fully or partially integrated in the same device as processing resource 272 or it can be separate but accessible to that device and processing resource 272. Thus, it is noted that the computing device 270 can be implemented on a support device and/or a collection of support devices, on a mobile device and/or a collection of mobile devices, and/or a combination of the support devices and the mobile devices.

The memory 276 can be in communication with the processing resource 272 via a communication link 274 (e.g., path). The communication link 274 can be local or remote to a computing device associated with the processing resource 272. Examples of a local communication link 274 can include an electronic bus internal to a computing device where the memory resource 276 is one of a volatile, non-volatile, fixed, and/or removable storage medium in communication with the processing resource 272 via the electronic bus.

Link 274 (e.g., local, wide area, regional, or global network) represents a cable, wireless, fiber optic, or remote connection via a telecommunication link, an infrared link, a radio frequency link, and/or other connectors or systems that provide electronic communication. That is, the link 274 can, for example, include a link to an intranet, the Internet, or a combination of both, among other communication interfaces. The link 274 can also include intermediate proxies, for example, an intermediate proxy server (not shown), routers, switches, load balancers, and the like.

The memory resource 276 can include a number of modules such as a heat module 278, a receive module 280, a determine module 282, and a heat module 284. The number of modules 278, 280, 282, 284 can include CRI that when executed by the processing resource 272 can perform a number of functions. The number of modules 278, 280, 282, 284 can be sub-modules of other modules. For example, the receive module 278 and the characterize module 280 can be sub-modules and/or contained within the same computing device. In another example, the number of modules 278, 280, 282, 284 can comprise individual modules at separate and distinct locations (e.g., CRM, etc.).

Each of the number of modules 278, 280, 282, 284 can include instructions that when executed by the processing resource 272 can function as a corresponding engine as described herein. For example, the determine module 282 can include CRI that when executed by the processing resource 272 can function as the determine engine 260. For instance, the determine module 282 can include CRI that when executed by the processing resource 232 can cause a computing device to determine whether any of the plurality of mapping signals exhibit a particular electrical pattern.

Embodiments are described herein of various apparatuses, systems, and/or methods. Numerous specific details are set forth to provide a thorough understanding of the overall structure, function, manufacture, and use of the embodiments as described in the specification and illustrated in the accompanying drawings. It will be understood by those skilled in the art, however, that the embodiments may be practiced without such specific details. In other instances, well-known operations, components, and elements have not been described in detail so as not to obscure the embodiments described in the specification. Those of ordinary skill in the art will understand that the embodiments described and illustrated herein are non-limiting examples, and thus it may be appreciated that the specific structural and functional details disclosed herein may be representative and do not necessarily limit the scope of the embodiments, the scope of which is defined solely by the appended claims.

Reference throughout the specification to "various embodiments," "some embodiments," "one embodiment," or "an embodiment", or the like, means that a particular feature, structure, or characteristic described in connection with the embodiment(s) is included in at least one embodiment. Thus, appearances of the phrases "in various embodiments," "in some embodiments," "in one embodiment," or "in an embodiment," or the like, in places throughout the specification, are not necessarily all referring to the same embodiment. Furthermore, the particular features, structures, or characteristics may be combined in any suitable manner in one or more embodiments. Thus, the particular features, structures, or characteristics illustrated or described in connection with one embodiment may be combined, in whole or in part, with the features, structures, or characteristics of one or more other embodiments without limitation given that such combination is not illogical or non-functional.

It will be appreciated that the terms "proximal" and "distal" may be used throughout the specification with reference to a clinician manipulating one end of an instrument used to treat a patient. The term "proximal" refers to the portion of the instrument closest to the clinician and the term "distal" refers to the portion located furthest from the clinician. It will be further appreciated that for conciseness and clarity, spatial terms such as "vertical," "horizontal," "up," and "down" may be used herein with respect to the illustrated embodiments. However, surgical instruments may be used in many orientations and positions, and these terms are not intended to be limiting and absolute.

Although at least one embodiment for thermal mapping catheter has been described above with a certain degree of particularity, those skilled in the art could make numerous alterations to the disclosed embodiments without departing from the spirit or scope of this disclosure. All directional references (e.g., upper, lower, upward, downward, left, right, leftward, rightward, top, bottom, above, below, vertical, horizontal, clockwise, and counterclockwise) are only used for identification purposes to aid the reader's understanding of the present disclosure, and do not create limitations, particularly as to the position, orientation, or use of the devices. Joinder references (e.g., affixed, attached, coupled, connected, and the like) are to be construed broadly and may include intermediate members between a connection of elements and relative movement between elements. As such, joinder references do not necessarily infer that two elements are directly connected and in fixed relationship to each other. It is intended that all matter contained in the above description or shown in the accompanying drawings shall be interpreted as illustrative only and not limiting. Changes in detail or structure may be made without departing from the spirit of the disclosure as defined in the appended claims.

Any patent, publication, or other disclosure material, in whole or in part, that is said to be incorporated by reference herein is incorporated herein only to the extent that the incorporated materials does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

What is claimed is:

1. A mapping and ablation catheter comprising:
   a catheter shaft comprising a proximal end and a distal end;
   a flexible framework coupled to the distal end of the catheter shaft at a proximal connector, wherein the flexible framework comprises six longitudinal arms extending distally from the proximal connector and arranged in a planar array, wherein each of the six longitudinally extending arms converge at a distal portion of the flexible framework to form three loops;
   a plurality of ring electrodes disposed on the flexible framework and configured to monitor mapping signals produced by a heart tissue, wherein the plurality of ring electrodes comprise greater than 32 ring electrodes disposed on the flexible framework;
   at least one additional electrode disposed on the distal end of the catheter shaft;
   a plurality of ablation electrodes disposed on the flexible framework, wherein the plurality of ablation electrodes are disposed at least one of longitudinally adjacent and transversely adjacent to one or more of the plurality of ring mapping electrodes in an alternating pattern; and
   an irrigation channel extending through the catheter shaft and an irrigation port disposed at the proximal connector at the distal end of the catheter shaft and in fluid communication with the irrigation channel, wherein a shape of the irrigation port is planar having a greater width than a height and configured to expel a fan shaped flow of fluid over the plurality of ring electrodes disposed on the flexible framework of three loops.

2. The mapping and ablation catheter of claim 1, wherein the at least one additional electrode comprises one or more ring electrodes.

3. The mapping and ablation catheter of claim 1, wherein a plane defined by a distal opening of the irrigation port is parallel with a plane defined by the planar array of the flexible framework.

4. The mapping and ablation catheter of claim 1, wherein the irrigation channel comprises a first irrigation lumen and a second irrigation lumen and the planar irrigation port comprises a first planar irrigation port in fluid communication with the first irrigation lumen and a second planar irrigation port in fluid communication with the second irrigation lumen, wherein the first and second irrigation ports are configured to expel fluid over each side of the flexible framework.

5. The mapping and ablation catheter of claim 1, wherein the plurality of ring mapping electrodes and the plurality of ablation electrodes are disposed on each of the six longitudinally extending arms in a longitudinally alternating pattern.

6. The mapping and ablation catheter of claim 1, wherein the plurality of ring electrodes are configured to receive a plurality of mapping signals during a defined time.

7. The mapping and ablation catheter of claim 1, wherein the plurality of ring mapping electrodes and the plurality of ablation electrodes are disposed on each of the six longitudinally extending arms in a transversely alternating pattern.

8. A mapping and ablation catheter system comprising:
   the mapping catheter of claim 1; and
   an energy source in communication with the plurality of ablation electrodes.

9. The mapping and ablation catheter system of claim 8, wherein the energy source is a radiofrequency (RF) generator configured to deliver RF energy to tissue via the plurality of ablation electrodes.

10. A mapping and ablation catheter system comprising: the mapping catheter of claim 1, and
a controller operably coupled with the plurality of ring electrodes and configured to determine whether any of the plurality of mapping signals exhibit a particular electrical pattern.

11. The mapping and ablation catheter system of claim 10, wherein controller is configured to apply a filter to one or more of the plurality of mapping signals in order to determine whether any of the plurality of mapping signals exhibit the particular electrical pattern.

\* \* \* \* \*